(12) United States Patent
Tajima

(10) Patent No.: US 10,595,804 B2
(45) Date of Patent: Mar. 24, 2020

(54) IMAGE PROCESSING APPARATUS, RADIOGRAPHY SYSTEM, IMAGE PROCESSING METHOD, AND IMAGE PROCESSING PROGRAM

(71) Applicant: FUJIFILM CORPORATION, Minato-ku, Tokyo (JP)

(72) Inventor: Takashi Tajima, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 119 days.

(21) Appl. No.: 15/974,720

(22) Filed: May 9, 2018

(65) Prior Publication Data
US 2018/0333118 A1    Nov. 22, 2018

(30) Foreign Application Priority Data

May 18, 2017 (JP) ................. 2017-099105

(51) Int. Cl.
*G06T 7/11* (2017.01)
*A61B 6/00* (2006.01)
(Continued)

(52) U.S. Cl.
CPC ............ *A61B 6/482* (2013.01); *A61B 6/4266* (2013.01); *A61B 6/505* (2013.01); *A61B 6/5217* (2013.01);
(Continued)

(58) Field of Classification Search
CPC ..... A61B 6/482; A61B 6/4266; A61B 6/5217; A61B 6/505; A61B 6/54; A61B 6/461; A61B 6/4035; A61B 6/548; A61B 6/4241; A61B 6/14; A61B 6/032; A61B 6/4405; A61B 6/5235; A61B 6/5241; A61B 5/055; A61B 5/4872; A61B 6/502; A61B 5/4035; A61B 6/469; A61B 6/563; A61B 5/0091; A61B 6/465; A61B 5/4509; A61B 5/7275; A61B 6/4014; A61B 6/52; A61B 5/1114; A61B 5/1128; A61B 5/742; A61B 6/00;
(Continued)

(56) References Cited

U.S. PATENT DOCUMENTS 5,852,647 A * 12/1998 Schick ............... A61B 6/482
                                              378/53
5,910,972 A *  6/1999 Ohkubo .............. G06T 5/50
                                              378/54
(Continued)

FOREIGN PATENT DOCUMENTS

JP        2011-56257 A      3/2011

*Primary Examiner* — Nimesh Patel
(74) *Attorney, Agent, or Firm* — Solaris Intellectual Property Group, PLLC

(57) ABSTRACT

A control unit acquires first radiographic image data and second radiographic image data and derives bone density from an image of a derivation region of a DXA image which is a difference image between a first radiographic image and a second radiographic image. Then, the control unit derives an evaluation value of the accuracy of derivation of the bone density, on the basis of at least one of the first radiographic image, the second radiographic image, and a bone part ES image, a soft part ES image, and a DXA image which are generated using the first radiographic image and the second radiographic image.

14 Claims, 14 Drawing Sheets

(51) Int. Cl.
*G06T 5/50* (2006.01)
*G06T 7/00* (2017.01)

(52) U.S. Cl.
CPC .............. *G06T 5/50* (2013.01); *G06T 7/0014* (2013.01); *G06T 7/11* (2017.01); *A61B 6/461* (2013.01); *A61B 6/54* (2013.01); *G06T 2207/10116* (2013.01); *G06T 2207/10152* (2013.01); *G06T 2207/20224* (2013.01); *G06T 2207/30008* (2013.01); *G06T 2207/30024* (2013.01)

(58) Field of Classification Search
CPC ................ A61B 6/464; A61B 17/1764; A61B 2017/568; A61B 2034/108; A61B 34/10; A61B 6/463; A61B 6/5205; G06T 7/0014; G06T 7/11; G06T 5/50; G06T 2207/10152; G06T 2207/10016; G06T 2207/30008; G06T 2207/20224; G06T 2207/33024; G06T 7/0012; G06T 2207/10116; G06T 2207/30012; G06T 2207/10081; G06T 2207/10088; G06T 2207/30004; G06T 2207/30036; G06T 2207/30101; G06T 7/12; G06T 7/55; G06T 7/97; G06T 2207/20132; G06T 2207/30068; G06T 7/60; G06T 17/00; G06T 19/20; G06T 2200/24; G06T 2210/41; G06T 2219/2004; G06T 2219/2021; G06T 7/0016; G06T 7/64; G01T 7/00; G01T 1/208; G01T 1/247; G01T 1/026; G01T 1/163; H04N 5/32; H04N 5/33; H04N 5/2253; H04N 5/23238; H04N 5/367; G01N 233/96494; G01N 2800/52; G01N 2223/419; G01N 2223/612; G01N 2223/6123; G01N 23/046; G01N 23/087; G01N 2800/2821; G01N 33/5023; G01N 33/6896; H01L 27/14658; H01L 31/115; H01L 27/146; H01L 27/14647; H01L 27/14676; H01L 31/085; H05G 1/00; H05G 1/06; H05G 1/08; H05G 1/10; A61F 2002/3008; A61F 2250/0098; A61F 2310/00011; A61F 2310/00179; A61F 2/28; A61F 2/32; A61F 2/44; A61F 2002/3096; A61F 2/30; A61F 2/38; A61F 2/30942; A61F 2/468; C07K 2319/02; C07K 14/4711; C07K 14/525; C12Q 1/6883; C12Q 1/6827; C12Q 2537/16; C12Q 2537/165; C12Q 1/6869; C12Q 2535/122

See application file for complete search history.

(56) References Cited

U.S. PATENT DOCUMENTS

| | | | | |
|---|---|---|---|---|
| 5,949,846 | A * | 9/1999 | Stein | A61B 6/505 378/198 |
| 6,031,892 | A * | 2/2000 | Karellas | A61B 6/06 250/370.09 |
| 6,574,302 | B2 * | 6/2003 | Adriaansz | A61B 6/032 378/18 |
| 6,853,741 | B1 * | 2/2005 | Ruth | G06T 7/0012 382/132 |
| 2001/0048732 | A1 * | 12/2001 | Wilson | A61B 6/06 378/21 |
| 2005/0096527 | A1 * | 5/2005 | Zeller | A61B 6/482 600/407 |

* cited by examiner

IMAGE PROCESSING APPARATUS, RADIOGRAPHY SYSTEM, IMAGE PROCESSING METHOD, AND IMAGE PROCESSING PROGRAM

CROSS-REFERENCE TO RELATED APPLICATION

This application claims priority under 35 USC 119 from Japanese Patent Application No. 2017-099105 filed May 18, 2017, the disclosure of which is incorporated by reference herein.

BACKGROUND

Technical Field

The present disclosure relates to an image processing apparatus, a radiography system, an image processing method, and an image processing program.

Related Art

In recent years, a technique has been known which derives at least one of the bone density or bone mineral content of a subject on the basis of the detection results of each radiation detector in a radiography apparatus including two radiation detectors that are stacked in a radiation emission direction and are irradiated with radiations having different energy levels (see JP2011-56257A). In the radiography apparatus, one radiation detector that is provided on the incident side of the radiation mainly absorbs a low-energy component of the radiation and generates image data of a radiographic image and the other radiation detector mainly absorbs a high-energy component of the radiation and generates image data of a radiographic image.

SUMMARY

In some cases, bone density and bone mineral content are derived using image data (for example, dual-energy X-ray absorptiometry (DXA) image data) which is generated on the basis of image data of two radiographic images generated by irradiation with (absorption of) radiations having different energy levels.

However, in a case in which bone density and bone mineral content are derived using the image data, the accuracy of derivation is likely to be reduced according to, for example, the state of the radiographic image.

The present disclosure has been made in view of the above-mentioned problems and an object of the present disclosure is to provide an image processing apparatus, a radiography system, an image processing method, and an image processing program that can improve the accuracy of derivation of at least one of bone density or bone mineral content.

In order to achieve the object, the present disclosure provides an image processing apparatus comprising: an acquisition unit that acquires a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted; a first derivation unit that derives at least one of bone density or bone mineral content from an image of a predetermined derivation region of a difference image between the first radiographic image and the second radiographic image; and a second derivation unit that derives an evaluation value of an accuracy of derivation of the at least one of the bone density or the bone mineral content derived by the first derivation unit, on the basis of a third radiographic image generated using the first radiographic image and the second radiographic image.

In order to achieve the object, the present disclosure provides an image processing apparatus comprising: an acquisition unit that acquires a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged; a first derivation unit that derives at least one of bone density or bone mineral content from an image of a predetermined derivation region of a difference image between the first radiographic image and the second radiographic image; and a second derivation unit that derives an evaluation value of an accuracy of derivation of the at least one of the bone density or the bone mineral content derived by the first derivation unit, on the basis of a third radiographic image generated using the first radiographic image and the second radiographic image.

In the image processing apparatus according to the present disclosure, the second derivation unit may derive the evaluation value on the basis of at least one of an index for evaluating noise which is superimposed on the image of the derivation region, an index for evaluating an influence of gas generated in a body of a subject, from which the at least one of the bone density or the bone mineral content is to be derived, on the image of the derivation region, or an index for evaluating an influence of scattered rays of the radiation on the image of the derivation region.

In the image processing apparatus according to the present disclosure, the first radiographic image and the second radiographic image may be corrected by correction data which is generated by irradiating the radiography apparatus with the radiation. The second derivation unit may derive the evaluation value on the basis of an imaging condition in a case in which the correction data is generated and an imaging condition in a case in which the first radiographic image and the second radiographic image are generated.

In the image processing apparatus according to the present disclosure, the imaging condition may be a position of a radiation source that irradiates the radiography apparatus with the radiation.

In the image processing apparatus according to the present disclosure, the second derivation unit may derive the evaluation value on the basis of an index for evaluating clarity of an outline of an image indicating a bone in the image of the derivation region.

The image processing apparatus according to the present disclosure may further comprise a display control unit that performs a control process of displaying the at least one of the bone density or the bone mineral content derived by the first derivation unit on a display unit in a case in which the evaluation value derived by the second derivation unit satisfies a condition indicating that the accuracy of derivation is high.

The image processing apparatus according to the present disclosure may further comprise a display control unit that performs a control process of displaying information indicating that the accuracy of derivation is low on a display unit in a case in which the evaluation value derived by the second derivation unit satisfies a condition indicating that the accuracy of derivation is low.

In the image processing apparatus according to the present disclosure, the display control unit may further perform a control process of displaying predetermined information for increasing the evaluation value on the display unit.

In the image processing apparatus according to the present disclosure, in a case in which the evaluation value derived by the second derivation unit satisfies a condition indicating that the accuracy of derivation is low, the first derivation unit may derive at least one of the bone density or the bone mineral content from an image of a derivation region which is different from the derivation region used to derive the at least one of the bone density or the bone mineral content and the second derivation unit may derive an evaluation value of the accuracy of derivation of the at least one of the bone density or the bone mineral content derived by the first derivation unit.

The image processing apparatus according to the present disclosure may further comprise a display control unit that performs a control process of displaying at least one of the bone density or the bone mineral content with a higher evaluation value among the evaluation values derived by the second derivation unit on the display unit.

In the image processing apparatus according to the present disclosure, the third radiographic image may be at least one of the difference image, a bone-part-highlighted image in which a bone tissue is highlighted, a soft-part-highlighted image in which a soft tissue is highlighted, the first radiographic image, or the second radiographic image.

In the image processing apparatus according to the present disclosure, each of the first and second radiation detectors may comprise a light emitting layer that is irradiated with the radiation and emits light. The plurality of pixels of each of the first and second radiation detectors may receive the light, generate the charge, and accumulate the charge. The light emitting layer of one of the first and second radiation detectors which is provided on an incident side of the radiation may include CsI and the light emitting layer of the other radiation detector may include GOS.

In order to achieve the object, the present disclosure provides a radiography system comprising: the image processing apparatus according to the present disclosure; and a radiography apparatus that outputs a first radiographic image and a second radiographic image to the image processing apparatus.

In order to achieve the object, the present disclosure provides an image processing method comprising: acquiring a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted; deriving at least one of bone density or bone mineral content from an image of a predetermined derivation region of a difference image between the first radiographic image and the second radiographic image; and deriving an evaluation value of an accuracy of derivation of the at least one of the bone density or the bone mineral content, on the basis of a third radiographic image generated using the first radiographic image and the second radiographic image.

In order to achieve the object, the present disclosure provides an image processing method comprising: acquiring a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged; deriving at least one of bone density or bone mineral content from an image of a predetermined derivation region of a difference image between the first radiographic image and the second radiographic image; and deriving an evaluation value of an accuracy of derivation of the at least one of the bone density or the bone mineral content, on the basis of a third radiographic image generated using the first radiographic image and the second radiographic image.

In order to achieve the object, the present disclosure provides a non-transitory recording medium recording an image processing program that causes a computer to perform: acquiring a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted; deriving at least one of bone density or bone mineral content from an image of a predetermined derivation region of a difference image between the first radiographic image and the second radiographic image; and deriving an evaluation value of an accuracy of derivation of the at least one of the bone density or the bone mineral content, on the basis of a third radiographic image generated using the first radiographic image and the second radiographic image.

In order to achieve the object, the present disclosure provides a non-transitory recording medium recording an image processing program that causes a computer to perform: acquiring a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged; deriving at least one of bone density or bone mineral content from an image of a predetermined derivation region of a difference image between the first radiographic image and the second radiographic image; and deriving an evaluation value of an accuracy of derivation of the at least one of the bone density or the bone mineral content, on the basis of a third radiographic image generated using the first radiographic image and the second radiographic image.

According to the present disclosure, it is possible to improve the accuracy of derivation of at least one of bone density or bone mineral content.

BRIEF DESCRIPTION OF THE DRAWINGS

Exemplary Embodiments of the present invention will be described in detail with reference to the following figures, wherein.

DETAILED DESCRIPTION

Hereinafter, embodiments of the present disclosure will be described in detail with reference to the drawings.

First Embodiment

Figure 1:
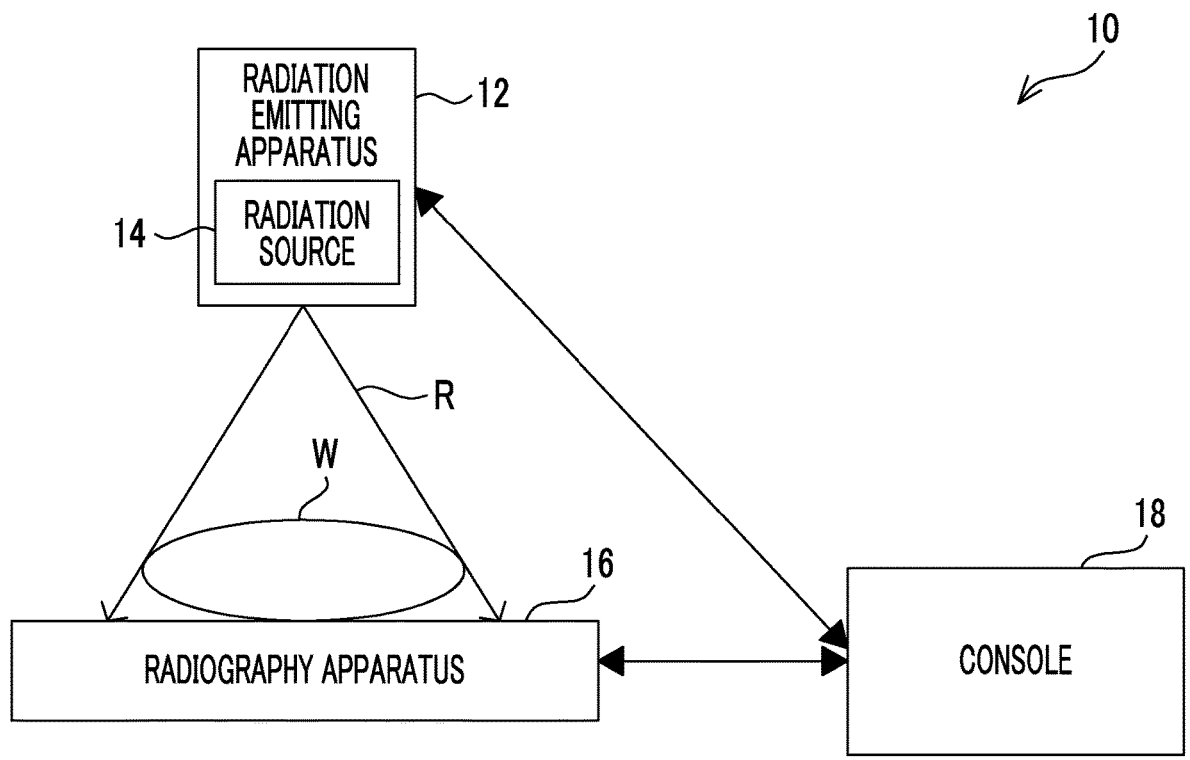
FIG. 1 is a block diagram illustrating an example of the configuration of a radiography system according to a first embodiment.

First, the configuration of a radiography system 10 according to this embodiment will be described with reference to FIG. 1. As illustrated in FIG. 1, the radiography system 10 includes a radiation emitting apparatus 12, a radiography apparatus 16, and a console 18. In this embodiment, the console 18 is an example of an image processing apparatus according to the present disclosure.

The radiation emitting apparatus 12 according to this embodiment includes a radiation source 14 that irradiates a subject W, which is an example of an imaging target, with radiation R such as X-rays. An example of the radiation emitting apparatus 12 is a treatment cart. A method for commanding the radiation emitting apparatus 12 to emit the radiation R is not particularly limited. For example, in a case in which the radiation emitting apparatus 12 includes an irradiation button, a user, such as a radiology technician, may press the irradiation button to command the emission of the radiation R such that the radiation R is emitted from the radiation emitting apparatus 12. In addition, for example, the user, such as a radiology technician, may operate the console 18 to command the emission of the radiation R such that the radiation R is emitted from the radiation emitting apparatus 12.

When receiving the command to emit the radiation R, the radiation emitting apparatus 12 emits the radiation R from the radiation source 14 according to set exposure conditions, such as a tube voltage, a tube current, and an irradiation period. Hereinafter, the dose of the radiation R is simply referred to as "the amount of radiation".

Figure 2:
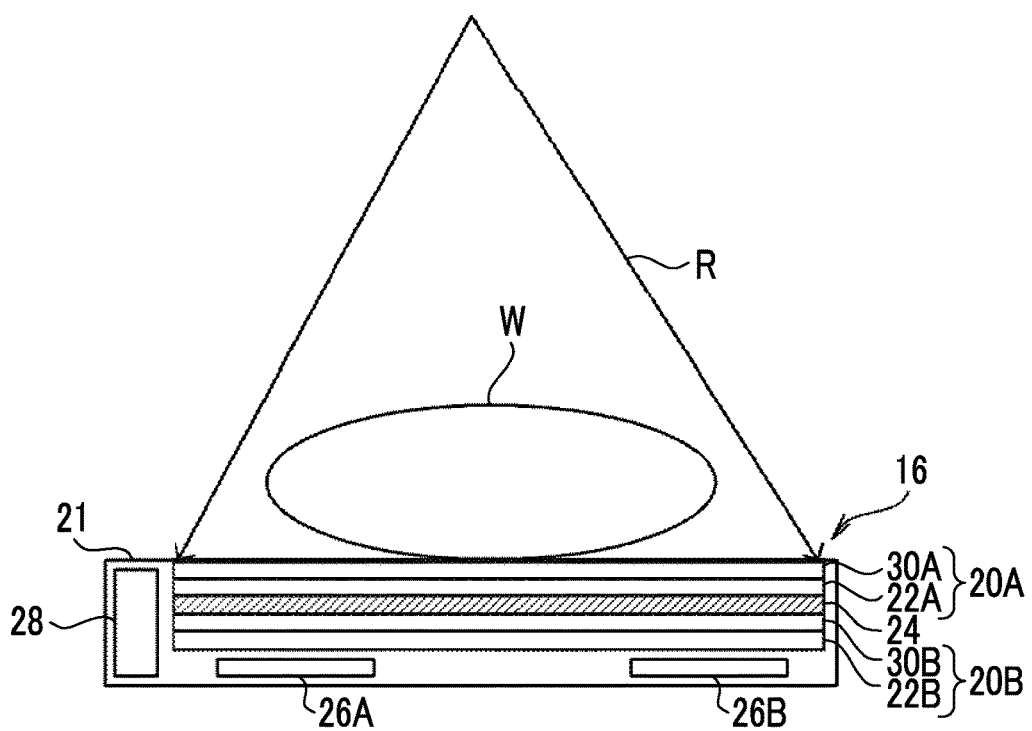
FIG. 2 is a side cross-sectional view illustrating an example of the configuration of a radiography apparatus according to the first embodiment.

Next, the configuration of the radiography apparatus 16 according to this embodiment will be described with reference to FIG. 2. As illustrated in FIG. 2, the radiography apparatus 16 includes a plate-shaped housing 21 that transmits the radiation R and has a waterproof, antibacterial, and airtight structure. The housing 21 includes a first radiation detector 20A and a second radiation detector 20B that detect the radiation R transmitted through the subject W. In addition, the housing 21 includes a radiation limitation member 24, a control substrate 26A, a control substrate 26B, and a case 28. The radiography apparatus 16 captures radiographic images of the subject W using the first radiation detector 20A and the second radiation detector 20B. Hereinafter, in a case in which the first radiation detector 20A and the second radiation detector 20B do not need to be distinguished from each other, they are generically referred to as "radiation detectors 20".

The first radiation detector 20A is provided on the incident side of the radiation R in the radiography apparatus 16 and the second radiation detector 20B is provided so as to be stacked on the side of the first radiation detector 20A from which the radiation R is transmitted and emitted. The first radiation detector 20A includes a thin film transistor (TFT) substrate 30A and a scintillator 22A which is an example of a light emitting layer that is irradiated with the radiation R and emits light. The TFT substrate 30A and the scintillator 22A are stacked in the order of the TFT substrate 30A and the scintillator 22A from the incident side of the radiation R. The term "stacked" means a state in which the first radiation detector 20A and the second radiation detector 20B overlap each other in a case in which the first radiation detector 20A and the second radiation detector 20B are seen from the incident side or the emission side of the radiation R in the radiography apparatus 16 and it does not matter how they overlap each other. For example, the first radiation detector 20A and the second radiation detector 20B, or the first radiation detector 20A, the radiation limitation member 24, and the second radiation detector 20B may overlap while coming into contact with each other or may overlap with a gap therebetween in the stacking direction.

The second radiation detector 20B includes a TFT substrate 30B and a scintillator 22B which is an example of the light emitting layer. The TFT substrate 30B and the scintillator 22B are stacked in the order of the TFT substrate 30B and the scintillator 22B from the incident side of the radiation R.

That is, the first radiation detector 20A and the second radiation detector 20B are so-called irradiation side sampling (ISS) radiation detectors that are irradiated with the radiation R from the side of the TFT substrates 30A and 30B.

In the radiography apparatus 16 according to this embodiment, the scintillator 22A of the first radiation detector 20A and the scintillator 22B of the second radiation detector 20B have different compositions. Specifically, for example, the scintillator 22A includes CsI (Tl) (cesium iodide having thallium added thereto) as a main component and the scintillator 22B includes gadolinium oxysulfide (GOS) as a main component. GOS has a higher sensitivity to the high-energy radiation R than CsI. In addition, a combination of the composition of the scintillator 22A and the composition of the scintillator 22B is not limited to the above-mentioned example and may be, for example, a combination of other compositions or a combination of the same compositions.

For example, the scintillators 22A and 22B have emission characteristics that vary depending on a thickness. As the thickness increases, the amount of light emitted increases and sensitivity increases. However, image quality deteriorates due to, for example, light scattering.

For example, in a case in which the scintillators 22A and 22B are formed by being filled with particles which are irradiated with the radiation R and emit light, such as GOS particles, as the diameter of the particle increases, the amount of light emitted increases and sensitivity increases. However, the amount of light scattering increases and the increase in the amount of light scattering affects adjacent pixels 32 (see FIG. 3), which results in the deterioration of image quality.

In addition, the scintillators 22A and 22B may have a stacked structure of a small-particle layer and a large-particle layer. For example, in a case in which each of the first radiation detector 20A and the second radiation detector 20B is irradiated with the radiation R from the scintillators 22A and 22B to the TFT substrates 30A and 30B unlike the radiography apparatus 16 according to this embodiment, image blurring is small in the scintillators 22A and 22B in which a region close to the irradiation side of the radiation R is filled with small particles and a region close to the side of the TFT substrate 30 that is the emission side of the radiation R is filled with large particles. However, oblique components of light that is radially emitted by the small particles are less likely to reach the TFT substrates 30A and 30B and sensitivity is reduced. In addition, in a case in which the ratio of the region filled with small particles to the region filled with large particles is changed such that the number of layers formed by the region filled with large particles is larger than the number of layers formed by the region filled with small particles, sensitivity increases. However, in this case, light scattering affects adjacent pixels 32, which results in the deterioration of image quality.

As the filling rate of the particles increases, the sensitivity of the scintillators 22A and 22B increases. However, the amount of light scattering increases and image quality deteriorates. Here, the filling rate is a value obtained by dividing the total volume of the particles of the scintillator 22A or 22B by the volume of the scintillator 22A or 22B and multiplying the divided value by 100 (the total volume of the particles of the scintillator 22A or 22B/the volume of the scintillator 22A or 22B×100). In addition, powder is treated in the scintillators 22A and 22B. Therefore, in a case in which the filling rate is greater than 80%, it is difficult to manufacture the scintillators 22A and 22B. For this reason, it is preferable that the filling rate is in the range of 50 vol % to 80 vol %.

In addition, the emission characteristics of the scintillators 22A and 22B vary depending on the doping amount of activator. As the doping amount of activator increases, the amount of light emitted tends to increase. However, the amount of light scattering increases and image quality deteriorates.

The emission characteristics of the scintillators 22A and 22B with respect to the radiation R vary depending on the material used for the scintillators 22A and 22B. For example, in a case in which each of the first radiation detector 20A and the second radiation detector 20B is irradiated with the radiation R from the scintillators 22A and 22B to the TFT substrates 30A and 30B unlike the radiography apparatus 16 according to this embodiment, the scintillator 22A is made of GOS and the scintillator 22B is made of CsI (Tl) in order to put emphasis on sensitivity in the scintillator 22A and to put emphasis on image quality in the scintillator 22B.

In addition, the emission characteristics of the scintillators 22A and 22B with respect to the radiation R vary depending on whether the scintillators 22A and 22B have a plate-shaped layer structure or a columnar separated layer structure.

For example, the scintillator 22A is configured to have the plate-shape layer structure and the scintillator 22B is configured to have the columnar separated layer structure in order to put emphasis on sensitivity in the scintillator 22A and to put emphasis on image quality in the scintillator 22B.

In a case in which reflecting layers that transmit the radiation R and reflect visible light are formed on the sides of the TFT substrates 30A and 30B which are opposite to the scintillators 22A and 22B, light generated by the scintillators 22A and 22B is more effectively guided to the TFT substrates 30A and 30B and sensitivity is improved. A method for forming the reflecting layer is not particularly limited. For example, any of a sputtering method, a vapor deposition method, and a coating method may be used to form the reflecting layer. It is preferable that the reflecting layer is made of a material with high reflectance in an emission wavelength region of the scintillators 22A and 22B used. For example, the reflecting layer is made of Au, Ag, Cu, Al, Ni, and Ti. For example, in a case in which the scintillators 22A and 22B are made of GOS:Tb, the reflecting layer is preferably made of Ag, Al, and Cu that have high reflectance in a wavelength of 400 nm to 600 nm. In a case in which the thickness of the reflecting layer is less than 0.01 μm, reflectance is not obtained. Even in a case in which the thickness is greater than 3 μm, the effect of further improving the reflectance is not obtained. For this reason, it is preferable that the thickness of the reflecting layer is in the range of 0.01 μm to 3 μm.

Therefore, the characteristics of the scintillators 22A and 22B may vary depending on a change in the diameter of particles, the multi-layered structure of the particles, the filling rate of the particles, the doping amount of activator, a material, a layer structure and the formation of the reflecting layer.

The radiation limitation member 24 that limits the transmission of the radiation R is provided between the first radiation detector 20A and the second radiation detector 20B. An example of the radiation limitation member 24 is a plate-shaped member made of, for example, copper or tin. It is preferable that a variation in the thickness of the radiation limitation member 24 in the incident direction of the radiation R is equal to or less than 1% in order to uniformize the limitation (transmittance) of the radiation. In a case in which the first radiation detector 20A sufficiently absorbs the radiation R, the radiation limitation member 24 may not be provided.

The control substrate 26A is provided so as to correspond to the first radiation detector 20A and electronic circuits, such as an image memory 56A and a control unit 58A which will be described below, are formed on the control substrate 26A. The control substrate 26B is provided so as to correspond to the second radiation detector 20B and electronic circuits, such as an image memory 56B and a control unit 58B which will be described below, are formed on the control substrate 26B. The control substrate 26A and the control substrate 26B are provided on the side of the second radiation detector 20B which is opposite to the incident side of the radiation R.

The case 28 is provided at a position (that is, outside the range of an imaging region) that does not overlap the radiation detector 20 at one end of the housing 21. For example, a power supply unit 70 which will be described below is accommodated in the case 28. The installation position of the case 28 is not particularly limited. For example, the case 28 may be provided at a position that overlaps the radiation detector 20 on the side of the second radiation detector 20B which is opposite to the incident side of the radiation R.

Next, the configuration of a main portion of an electric system of the radiography apparatus 16 according to this embodiment will be described with reference to FIG. 3.

Figure 3:
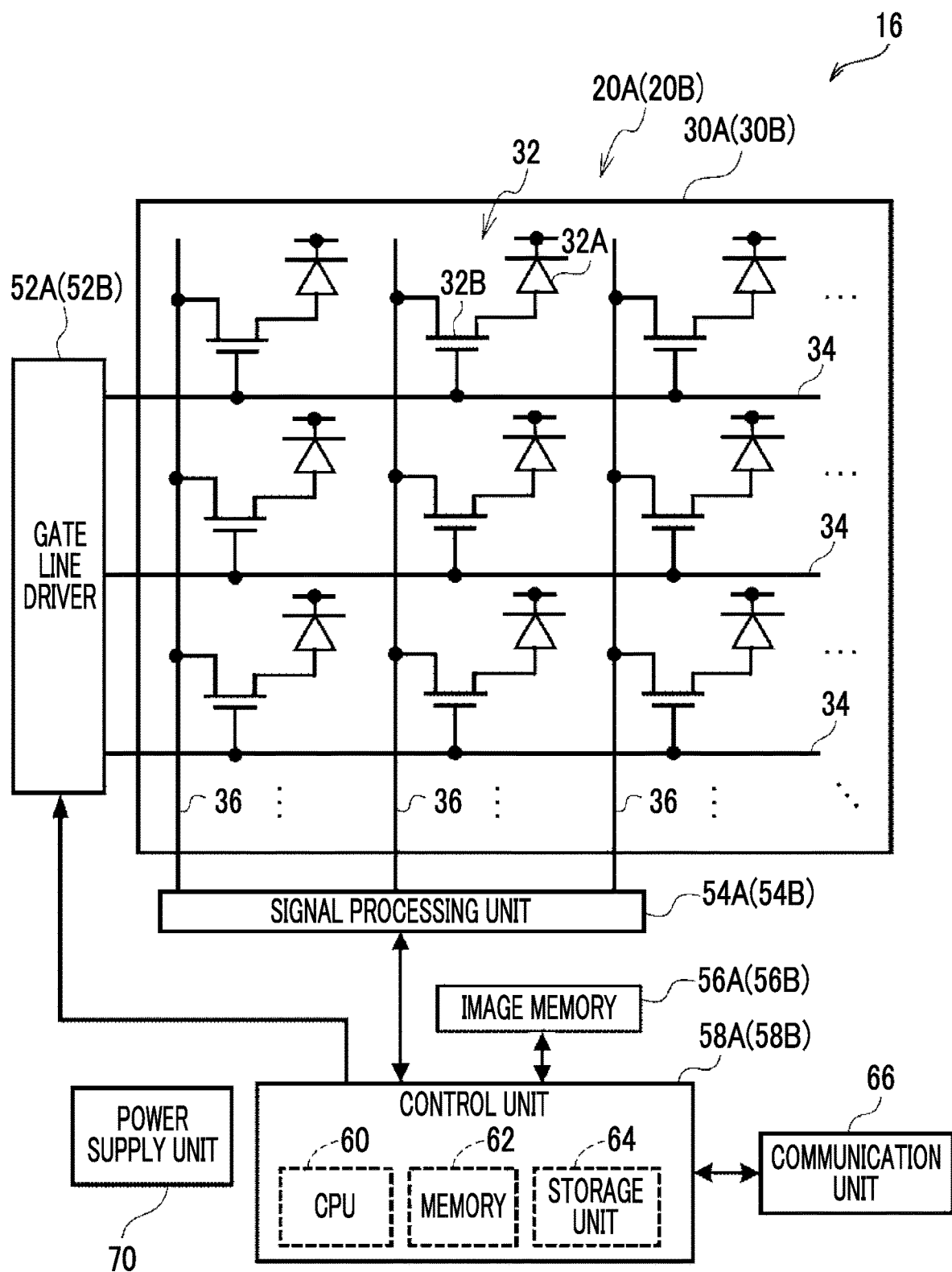
FIG. 3 is a block diagram illustrating an example of the configuration of a main portion of an electric system of the radiography apparatus according to the first embodiment.

As illustrated in FIG. 3, a plurality of pixels 32 are two-dimensionally provided in one direction (a row direction in FIG. 3) and a cross direction (a column direction in FIG. 3) that intersects the one direction on the TFT substrate 30A. The pixel 32 includes a sensor unit 32A and a field effect thin film transistor (TFT; hereinafter, simply referred to as a "thin film transistor") 32B.

The sensor unit 32A includes, for example, an upper electrode, a lower electrode, and a photoelectric conversion film which are not illustrated, absorbs the light emitted from the scintillator 22A, generates charge, and accumulates the generated charge. The thin film transistor 32B reads the charge accumulated in the sensor unit 32A, converts the charge into an electric signal, and outputs the electric signal in response to a control signal. The sensor unit 32A is an example of a conversion element that generates a larger amount of charge as the amount of radiation becomes larger.

A plurality of gate lines 34 which extend in the one direction and are used to turn on and off each thin film transistor 32B are provided on the TFT substrate 30A. In addition, a plurality of data lines 36 which extend in the cross direction and are used to read out the charge through the thin film transistors 32B in an on state are provided on the TFT substrate 30A.

A gate line driver 52A is provided on one side of two adjacent sides of the TFT substrate 30A and a signal processing unit 54A is provided on the other side. Each gate line 34 of the TFT substrate 30A is connected to the gate line driver 52A and each data line 36 of the TFT substrate 30A is connected to the signal processing unit 54A.

The thin film transistors 32B corresponding to each gate line 34 on the TFT substrate 30A are sequentially turned on (in units of rows illustrated in FIG. 3 in this embodiment) by control signals which are supplied from the gate line driver 52A through the gate lines 34. Then, the charge which has been read by the thin film transistor 32B in an on state is transmitted as an electric signal through the data line 36 and is input to the signal processing unit 54A. In this way, charge is sequentially read from each gate line 34 (in units of rows illustrated in FIG. 3 in this embodiment) and image data indicating a two-dimensional radiographic image is acquired.

The signal processing unit 54A includes amplifying circuits (not illustrated) for amplifying an input electric signal and sample-and-hold circuits (not illustrated) which are provided for each data line 36. The electric signal transmitted through each data line 36 is amplified by the amplifying circuit and is then held by the sample-and-hold circuit. A multiplexer and an analog/digital (A/D) converter are connected to the output side of the sample-and-hold circuit in this order. The electric signals held by each sample-and-hold circuit are sequentially (serially) input to the multiplexer and are sequentially selected by the multiplexer. Then, the selected electric signal is converted into digital image data by the A/D converter.

The control unit 58A which will be described below is connected to the signal processing unit 54A. The image data output from the A/D converter of the signal processing unit 54A is sequentially output to the control unit 58A. The image memory 56A is connected to the control unit 58A. The image data sequentially output from the signal processing unit 54A is sequentially stored in the image memory 56A under the control of the control unit 58A. The image memory 56A has memory capacity that can store a predetermined amount of image data. Whenever a radiographic image is captured, captured image data is sequentially stored in the image memory 56A.

The control unit 58A includes a central processing unit (CPU) 60, a memory 62 including, for example, a read only memory (ROM) and a random access memory (RAM), and a non-volatile storage unit 64 such as a flash memory. An example of the control unit 58A is a microcomputer.

A communication unit 66 is connected to the control unit 58A and transmits and receives various kinds of information to and from external apparatuses, such as the radiation emitting apparatus 12 and the console 18, using at least one of wireless communication or wired communication. The power supply unit 70 supplies power to each of the above-mentioned various circuits or elements (for example, the gate line driver 52A, the signal processing unit 54A, the image memory 56A, the control unit 58A, and the communication unit 66). In FIG. 3, lines for connecting the power supply unit 70 to various circuits or elements are not illustrated in order to avoid complication.

Components of the TFT substrate 30B, the gate line driver 52B, the signal processing unit 54B, the image memory 56B, and the control unit 58B of the second radiation detector 20B have the same configurations as the corresponding components of the first radiation detector 20A and thus the description thereof will not be repeated here. In addition, the control unit 58A and the control unit 58B are connected such that they can communicate with each other.

With the above-mentioned configuration, the radiography apparatus 16 according to this embodiment captures radiographic images using the first radiation detector 20A and the second radiation detector 20B. Hereinafter, the radiographic image captured by the first radiation detector 20A is referred to as a "first radiographic image" and image data indicating the first radiographic image is referred to as "first radiographic image data". In addition, hereinafter, the radiographic image captured by the second radiation detector 20B is referred to as a "second radiographic image" and image data indicating the second radiographic image is referred to as "second radiographic image data".

Figure 4:
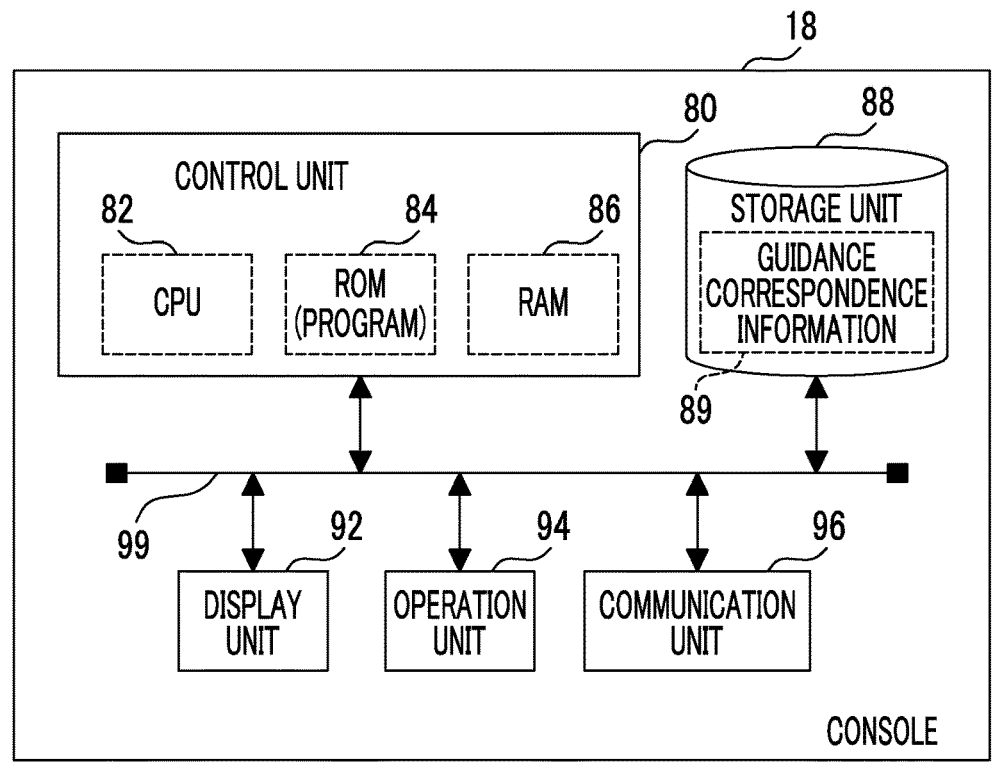
FIG. 4 is a block diagram illustrating an example of the configuration of a main portion of an electric system of a console according to the first embodiment.

Next, the configuration of the console 18 according to this embodiment will be described with reference to FIG. 4. As illustrated in FIG. 4, the console 18 includes a control unit 80. The control unit includes a CPU 82 that controls the overall operation of the console 18, a ROM 84 in which, for example, various programs or various parameters are stored in advance, and a RAM 86 that is used as, for example, a work area when the CPU 82 executes various programs.

In addition, the console 18 includes a non-volatile storage unit 88 such as a hard disk drive (HDD). The storage unit 88 stores and holds image data indicating the radiographic image captured by the first radiation detector 20A, image data indicating the radiographic image captured by the second radiation detector 20B, and various other data items. In addition, in this embodiment, the storage unit 88 stores information (hereinafter, referred to as "guidance correspondence information") 89 indicating a correspondence relationship between an evaluation item and guidance information in advance, which will be described in detail below.

The console 18 further includes a display unit 92, an operation unit 94, and a communication unit 96. The display unit 92 displays, for example, information related to imaging and a captured radiographic image. The operation unit 94 is used by a user to input a command to capture a radiographic image and a command to perform image processing for the captured radiographic image. For example, the operation unit 94 may have the form of a keyboard or the form of a touch panel integrated with the display unit 92. The communication unit 96 transmits and receives various kinds of information to and from the radiography apparatus 16 and the radiation emitting apparatus 12, using at least one of wireless communication or wired communication. In addition, the communication unit 96 transmits and receives various kinds of information to and from the external systems, such as a picture archiving and communication system (PACS) and a radiology information system (RIS), using at least one of wireless communication or wired communication.

The control unit 80, the storage unit 88, the display unit 92, the operation unit 94, and the communication unit 96 are connected to each other through a bus 99.

In the radiography apparatus 16 according to this embodiment, since the first radiation detector 20A and the radiation limitation member 24 absorb the radiation R, the amount of radiation that reaches the second radiation detector 20B is less than the amount of radiation that reaches the first radiation detector 20A. In addition, the radiation limitation member 24 generally has the characteristic that it absorbs a larger number of soft-ray components than hard-ray components in energy forming the radiation R, which depends on the material forming the radiation limitation member 24. Therefore, the energy distribution of the radiation R that reaches the second radiation detector 20B has a larger number of hard-ray components than the energy distribution of the radiation R that reaches the first radiation detector 20A.

In this embodiment, for example, about 50% of the radiation R that has reached the first radiation detector 20A is absorbed by the first radiation detector 20A and is used to capture a radiographic image. In addition, about 60% of the radiation R that has passed through the first radiation detector 20A and reached the radiation limitation member 24 is absorbed by the radiation limitation member 24. About 50% of the radiation R that has passed through the first radiation detector 20A and the radiation limitation member 24 and reached the second radiation detector 20B is absorbed by the second radiation detector 20B and is used to capture a radiographic image. Since the absorptivity of radiation by the radiation detector 20 and the radiation limitation member 24 varies depending on the energy of the radiation R, the shape of a spectrum changes.

That is, the amount of radiation used by the second radiation detector 20B to capture a radiographic image is about 20% of the amount of radiation used by the first radiation detector 20A to capture a radiographic image. In addition, the ratio of the amount of radiation used by the second radiation detector 20B to capture a radiographic image to the amount of radiation used by the first radiation detector 20A to capture a radiographic image is not limited to the above-mentioned ratio. However, it is preferable that the amount of radiation used by the second radiation detector 20B to capture a radiographic image is equal to or greater than 10% of the amount of radiation used by the first radiation detector 20A to capture a radiographic image in terms of diagnosis.

Figure 5:
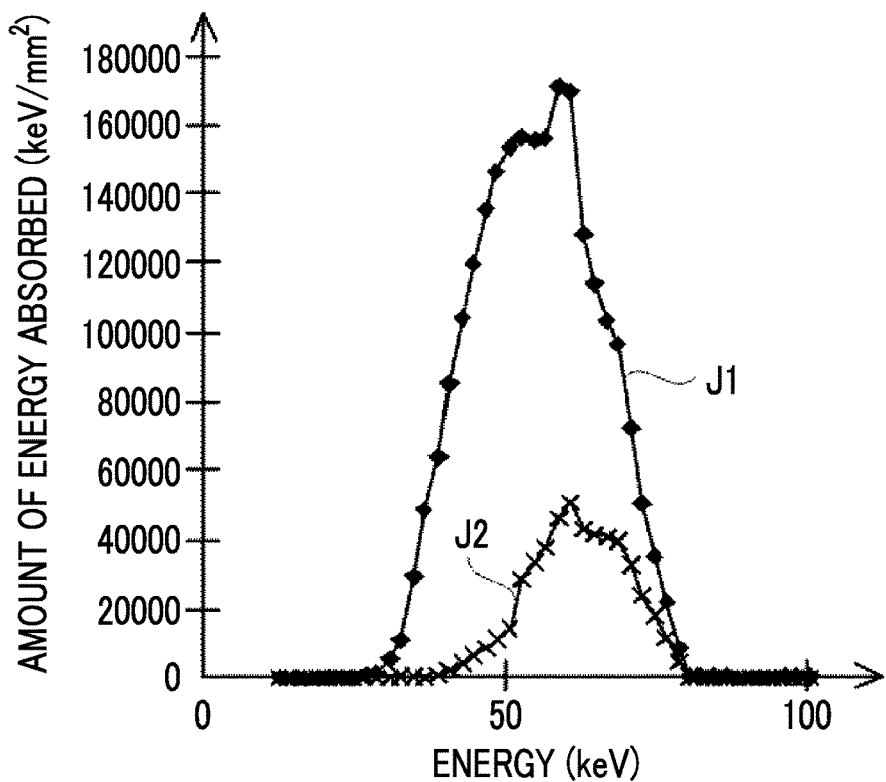
FIG. 5 is a graph illustrating the amount of radiation that reaches each of a first radiation detector and a second radiation detector.

Low-energy components of the radiation R are absorbed first. The radiation R absorbed by each of the first radiation detector 20A and the second radiation detector 20B will be described with reference to FIG. 5. In FIG. 5, the vertical axis indicates the amount of radiation R absorbed per unit area and the horizontal axis indicates the energy of the radiation R in a case in which the tube voltage of the radiation source 14 is 80 kV. In addition, in FIG. 5, a solid line J1 indicates the relationship between the energy of the radiation R absorbed by the first radiation detector 20A and the amount of radiation R absorbed per unit area. In addition, in FIG. 5, a solid line J2 indicates the relationship between the energy of the radiation R absorbed by the second radiation detector 20B and the amount of radiation R absorbed per unit area. Since the low-energy components of the radiation R are absorbed first, for example, as illustrated in FIG. 5, the energy components of the radiation R that reaches the second radiation detector 20B do not include the low-energy components of the energy components of the radiation R that reaches the first radiation detector 20A. That is, the energy of the radiation R emitted to the first radiation detector 20A is different from the energy of the radiation R emitted to the second radiation detector 20B through the first radiation detector 20A. Therefore, in the radiography apparatus 16 according to this embodiment, the radiation detectors 20 are irradiated with the radiations R having different energy levels and radiographic images are generated by the radiation detectors 20.

The console 18 according to this embodiment acquires radiographic image data generated by the radiation detectors 20 irradiated with the radiations R having different energy levels (radiation R with a first energy level and radiation R with a second energy level). In addition, the console 18 derives the ratio of the values of the corresponding pixels of first radiographic image data and second radiographic image data and generates image data for deriving the bone density of the subject W. Hereinafter, the image data for deriving the bone density of the subject W is referred to as "dual-energy X-ray absorptiometry (DXA) image data" and an image indicated by the DXA image data is referred to as a "DXA image". Specifically, the console 18 performs log conversion for each pixel value of each of the first radiographic image data and the second radiographic image data. Then, the console 18 subtracts image data obtained by performing log conversion for the second radiographic image data from image data obtained by performing log conversion for the first radiographic image data for each corresponding pixel to generate DXA image data. The DXA image according to this embodiment is an example of a difference image and a third radiographic image according to the present disclosure.

Figure 6:
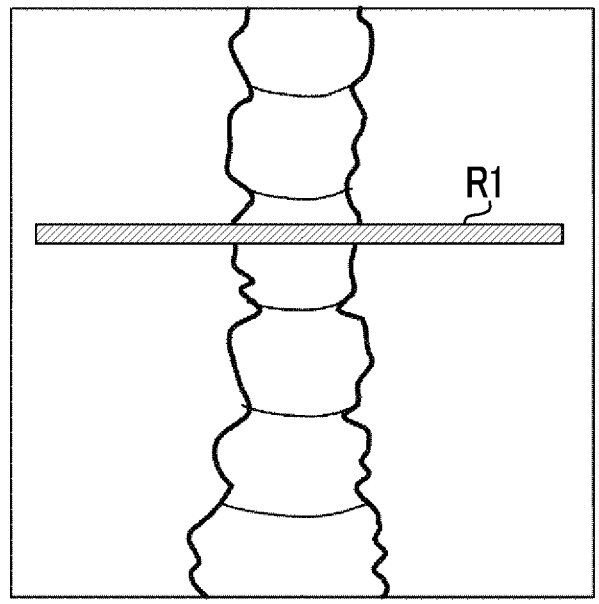
FIG. 6 is a front view illustrating an example of a region from which a DXA profile used to derive bone density is to be derived.

In addition, for example, as illustrated in FIG. 6, the console 18 according to this embodiment derives bone density from each pixel value (that is, the ratio of the values of the corresponding pixels of the first radiographic image and the second radiographic image) of the bone of the subject W in the cross-sectional direction (the horizontal direction in the example illustrated in FIG. 6) in the DXA image.

Figure 7:
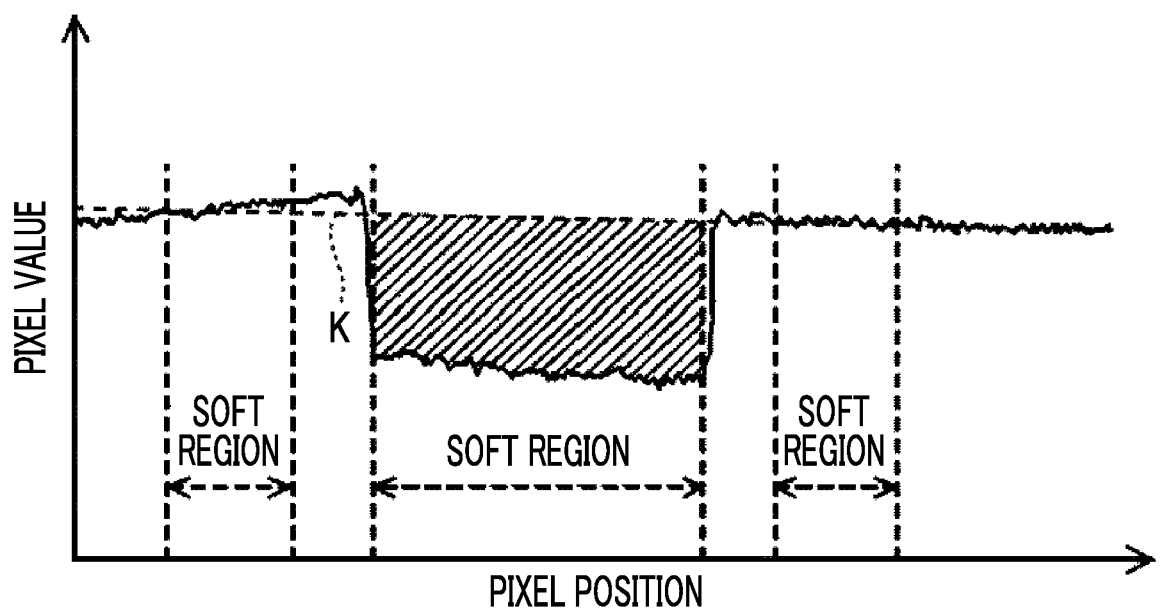
FIG. 7 is a graph illustrating a bone density derivation process.

FIG. 7 illustrates the value of each pixel in a derivation region R1 of the DXA image illustrated in FIG. 6. In FIG. 7, the horizontal axis indicates a pixel position in the horizontal direction of FIG. 6. In addition, in FIG. 7, the vertical axis indicates an average value of the values of a plurality of pixels in the vertical direction of FIG. 6 at each pixel position in the horizontal direction of FIG. 6. Hereinafter, a data group of the pixel values at each pixel position along the horizontal direction of FIG. 6 which is illustrated in FIG. 7 is referred to as a "DXA profile".

As illustrated in FIG. 7, for the pixel values in the DXA profile, a pixel value at a pixel position corresponding to the bone tissue of the subject W is less than a pixel value at a pixel position corresponding to the soft tissue. The console 18 according to this embodiment derives the average value of the pixel values in soft tissue regions (hereinafter, referred to as "soft regions") on both sides of a bone tissue region (hereinafter, referred to as a "bone region") and derives a straight line (hereinafter, referred to as a "reference line") K that connects the average values derived at the pixel positions in a central portion of each soft region. In addition, the console 18 adds the differences between the reference line K and the pixel values at each pixel position in the bone region to derive the area of the bone region (the area of a hatched portion illustrated in FIG. 7). The area is a value corresponding to the bone mass of the subject W. For example, the bone region is separated from the soft region by a predetermined number of pixels in FIG. 7 in order to prevent the influence of noise caused by rays scattered by the bone.

In addition, the console 18 divides the derived area by the number of pixels corresponding to the width of the bone region to derive the difference between the pixel values of the bone region and the soft region per unit number of pixels. The difference is a value corresponding to the bone density of the subject W. Then, the console 18 multiplies the derived difference between the pixel values of the bone region and the soft region per unit number of pixels by a predetermined unit conversion coefficient to derive the bone density of the subject W. In this embodiment, the pixel position of the derivation region R1 used to derive the DXA profile in the DXA image data, the pixel position of the soft region in the DXA profile, and the pixel position of the bone region are predetermined according to, for example, the subject W and an imaging part.

In some cases, in the derivation of the bone density, for example, the accuracy of derivation of the bone density is reduced in a case in which noise is superimposed on the image of the derivation region R1 or a case in which gas generated in the body of the subject W (hereinafter, simply referred to as "gas") is included in the image of the derivation region R1 (which will be described in detail below). As a result, the desired accuracy is not obtained. In this embodiment, "a state in which noise is superimposed on an image" includes, for example, a state in which noise is superimposed on image data indicating a radiographic image, such as the first radiographic image data or the second radiographic image data, by the influence of disturbance and the influence of noise appears in the image indicated by the image data and a state in which a sufficiently high signal/noise (S/N) ratio is not obtained since the amount of radiation R is small.

For this reason, in this embodiment, the console 18 displays an evaluation value for evaluating the accuracy of derivation of the bone density on the display unit 92. In a case in which the accuracy of derivation does not reach the desired accuracy, the console 18 performs a process for improving the accuracy of derivation to improve the accuracy of derivation of the bone density.

Next, the operation of the console 18 according to this embodiment in a case in which bone density is derived will be described.

Figure 8:
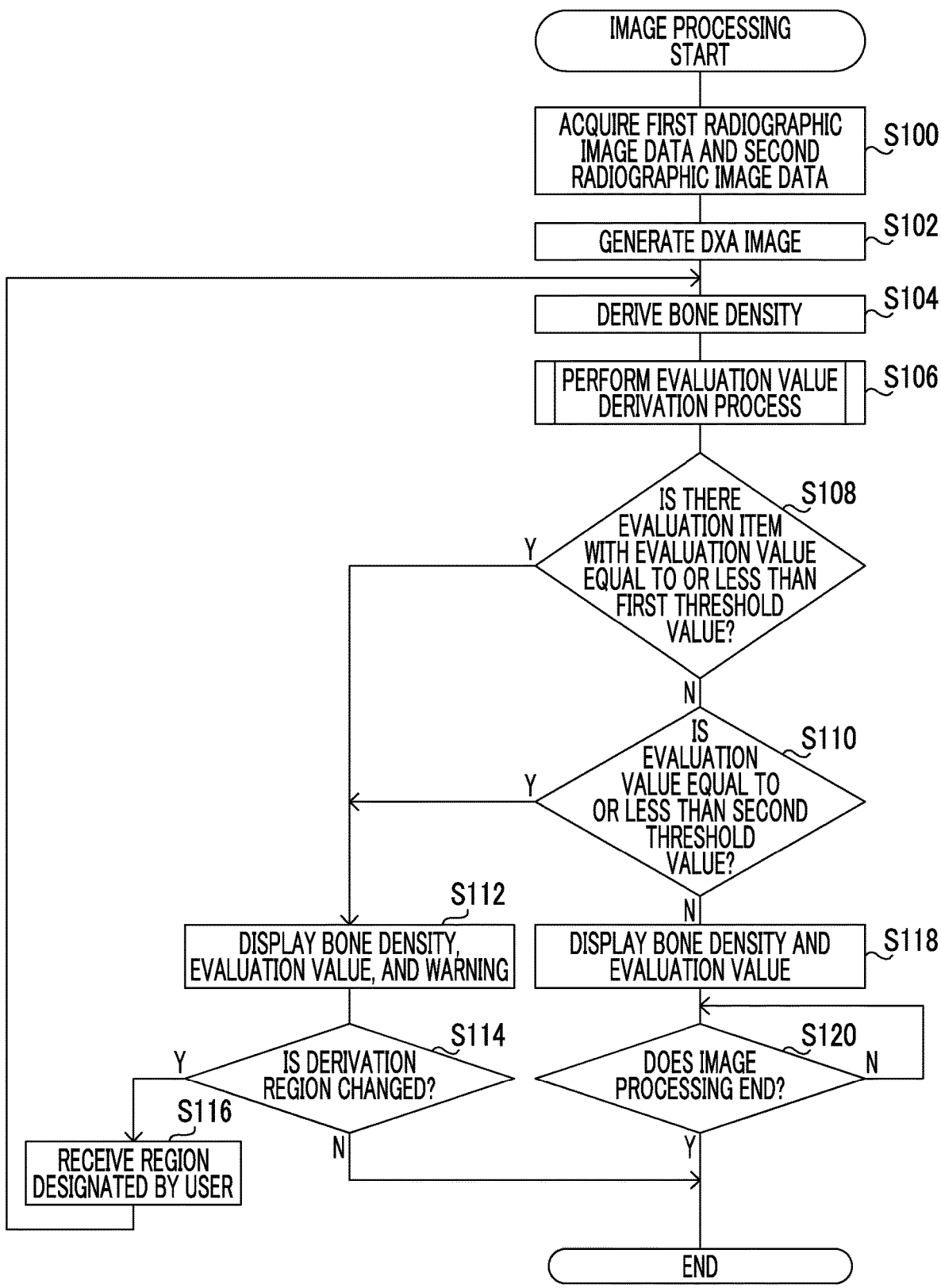
FIG. 8 is a flowchart illustrating an example of the flow of image processing performed by a control unit of the console according to the first embodiment.

FIG. 8 is a flowchart illustrating an example of the flow of image processing performed by the control unit 80 of the console 18 according to this embodiment. In a case in which the user inputs a command to derive bone density through the operation unit 94, the control unit 80 of the console 18 according to this embodiment executes an image processing program stored in the ROM 84 to perform the image processing illustrated in FIG. 8. In addition, in a case in which the CPU 82 of the control unit 80 according to this embodiment executes the image processing program, the control unit 80 according to this embodiment functions as an example of an acquisition unit, a first derivation unit, a second derivation unit, and a display control unit according to the present disclosure.

In Step S100 of FIG. 8, the control unit 80 acquires first radiographic image data and second radiographic image data. The acquisition destination of the first radiographic image data and the second radiographic image data is not particularly limited. For example, in a case in which the first radiographic image data and the second radiographic image data received from the radiography apparatus 16 have been stored in the storage unit 88 in advance, the control unit 80 may acquire the first radiographic image data and the second radiographic image data from the storage unit 88. In addition, for example, the control unit 80 may directly acquire the first radiographic image data and the second radiographic image data from the radiography apparatus 16.

In this embodiment, information indicating an imaging part is associated with the first radiographic image and the second radiographic image. The control unit 80 acquires the information indicating the imaging part, in addition to the first radiographic image data and the second radiographic image data.

Then, in Step S102, as described above, the control unit 80 generates DXA image data (DXA image) using the first radiographic image data and the second radiographic image. Then, in Step S104, the control unit 80 derives bone density using the DXA image, as described above.

Figure 9:
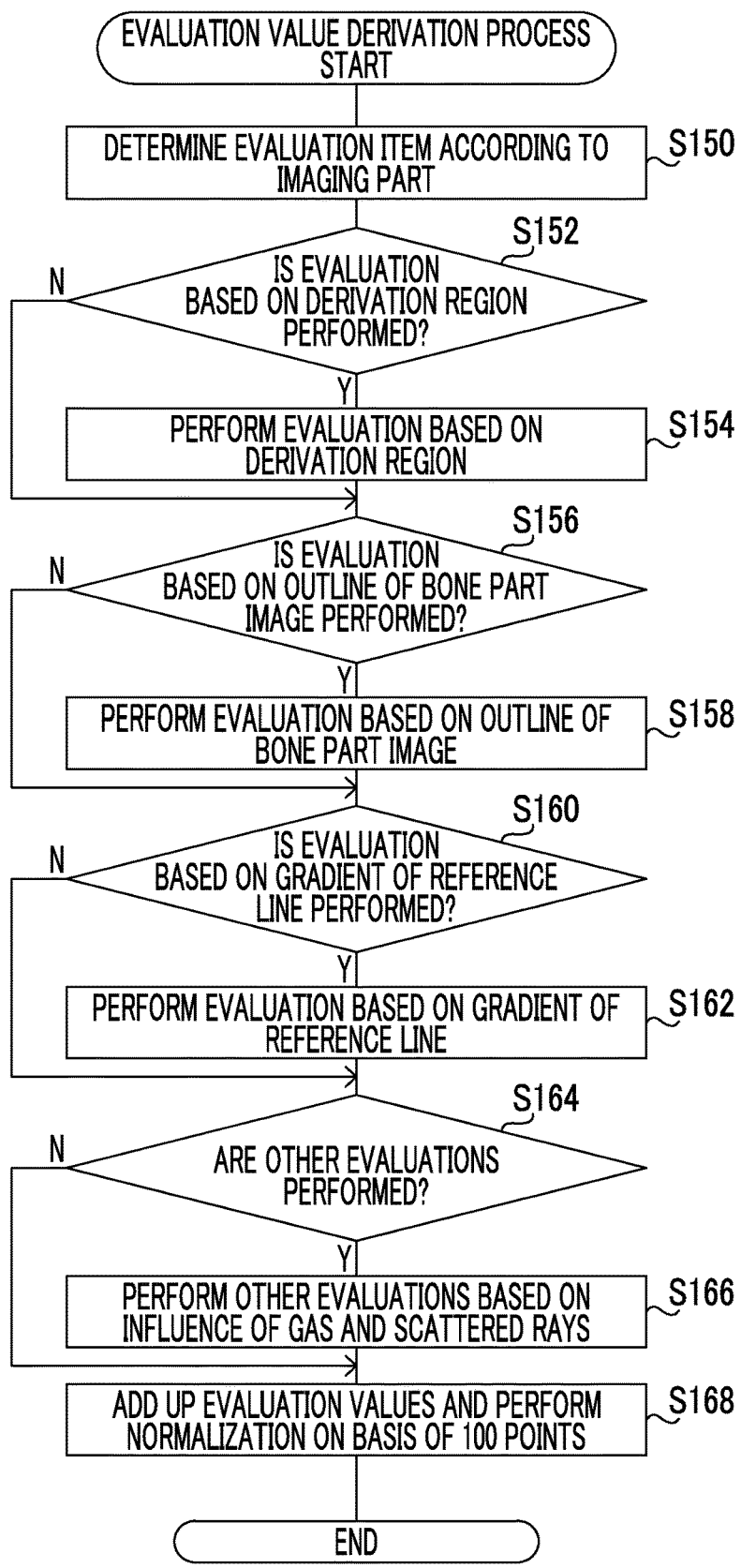
FIG. 9 is a flowchart illustrating an example of the flow of an evaluation value derivation process performed by the control unit of the console according to the first embodiment.

Then, in Step S106, the control unit 80 performs an evaluation value derivation process. FIG. 9 is a flowchart illustrating an example of the flow of the evaluation value derivation process performed by the control unit 80 according to this embodiment.

In Step S150 of FIG. 9, the control unit 80 determines an evaluation item according to an imaging part. In this embodiment, the following four evaluation items are used as the evaluation items for deriving the evaluation value.

A first evaluation item is evaluation based on the derivation region R1. In some cases, the image of the derivation region R1 is affected by, for example, noise or gas. Therefore, the influence of the noise and the gas is evaluated from the image of the derivation region R1.

A second evaluation item is evaluation based on the outline of the image of the bone tissue (hereinafter, referred to as a "bone part image").

In a case in which the outline of the bone part image is not clear, for example, the range of the bone region in the DXA profile is likely to be affected by noise superimposed on the image. Therefore, the influence of noise is evaluated from the DXA image (or the image of the derivation region R1).

A third evaluation item is evaluation based on the gradient of the reference line K (whether the pixel value is regarded as a constant value). In some cases, the gradient of the reference line K is affected by, for example, gas or scattered rays. Therefore, the influence of gas or scattered rays is evaluated from the image of the derivation region R1.

A fourth evaluation item is other predetermined evaluations. In addition to the three evaluation items, for example, the influence of noise or gas is likely to appear in the image of the derivation region R1 or the DXA profile. The influence of noise or gas is evaluated by a method different from those used for the three evaluation items on the basis of, for example, the image of the derivation region R1 or the DXA profile (a specific example of the method will be described in detail below).

In this embodiment, which of the evaluation items evaluation is performed for is predetermined according to the imaging part. In addition, information indicating the correspondence relationship between the imaging part and the evaluation item for deriving the evaluation value may be stored in the storage unit 88 in advance or may be acquired from an external system or apparatus. Furthermore, the user may designate the correspondence relationship between the imaging part and the evaluation item for deriving the evaluation value through the operation unit 94.

The evaluation value may be determined by a point addition method, a point subtraction method, or a combination of the point addition method and the point subtraction method. In this embodiment, for example, as the evaluation value increases, the accuracy of derivation increases.

Then, in Step S152, the control unit 80 determines whether to perform the evaluation based on the derivation region R1 which is the first evaluation item, on the basis of the evaluation item determined in Step S150. In a case in which the evaluation based on the derivation region R1 is not performed, the determination result in Step S152 is "No" and the process proceeds to Step S156. On the other hand, in a case in which the evaluation based on the derivation region R1 is performed, the determination result in Step S152 is "Yes" and the process proceeds to Step S154.

In Step S154, the control unit 80 derives the evaluation value from the derivation region R1.

Figure 10:
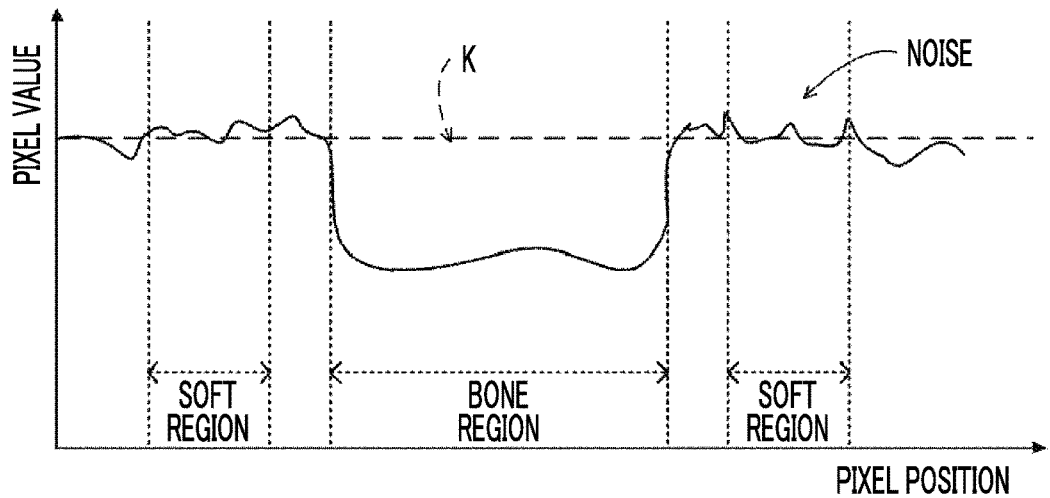
FIG. 10 is a graph illustrating an example of a DXA profile and a reference line in a case in which noise is superimposed.

In a case in which noise is superimposed on the image of the derivation region R1, for example, the pixel value of the DXA profile varies as illustrated in FIG. 10. In a case in which the pixel value of the DXA profile varies, it is difficult to appropriately derive the reference line K. As a result, the accuracy of derivation of the bone density is reduced. Therefore, there is a correspondence relationship between the standard deviation of the pixel value of the image of the derivation region R1 and the amount of noise superimposed. For example, in this embodiment, the correspondence relationship between the standard deviation of the pixel value of the image of the derivation region R1 and the evaluation value is obtained in advance. The control unit 80 calculates the standard deviation of the pixel value of the image of the derivation region R1 and derives an evaluation value corresponding to the calculated standard deviation, using the correspondence relationship between the standard deviation of the pixel value of the image of the derivation region R1 and the evaluation value. In this embodiment, the evaluation value is derived using the image of the derivation region R1 in the DXA image. However, the evaluation value may be derived using an image corresponding to the derivation region R1 of other images. For example, the evaluation value may be derived using an image corresponding to the derivation region R1 of the first radiographic image. In addition, the correspondence relationship between the standard deviation of the pixel value of the image of the derivation region R1 and the evaluation value in this embodiment is an example of an index for evaluating noise superimposed on the image of the derivation region according to the present disclosure.

Figure 11:
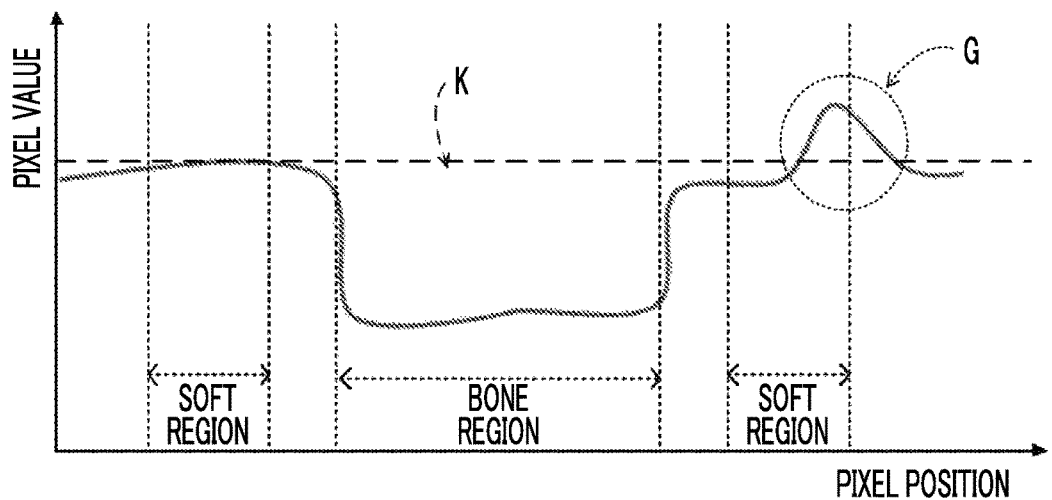
FIG. 11 is a graph illustrating an example of the DXA profile and the reference line in a case in which a gas region is included.

In a case in which gas is included in the image of the derivation region R1 (the image of gas is included), for example, a protruding gas region G with a larger width than that in a case in which noise is superimposed is generated in the DXA profile, as illustrated in FIG. 11. As the pixel value of the gas region G, the width of the region, and the number of gas regions increase, the accuracy of derivation of the bone density is reduced. For this reason, for example, in this embodiment, a correspondence relationship among the width of the gas region G, the number of gas regions G, and the evaluation value is obtained in advance. The control unit 80 detects the width of the gas region G and the number of gas regions G from the image of the derivation region R1 and derives an evaluation value corresponding to the detected width of the gas region G and the detected number of gas regions G, using the correspondence relationship among the width of the gas region G, the number of gas regions G, and the evaluation value. In this embodiment, the evaluation value is derived using the image of the derivation region R1 in the DXA image. However, the evaluation value may be derived using an image corresponding to the derivation region R1 in other images. For example, the evaluation value may be derived using an image corresponding to the derivation region R1 of the first radiographic image. In addition, the correspondence relationship among the width of the gas region G, the number of gas regions G, and the evaluation value in this embodiment is an example of an index for evaluating the influence of gas generated in the body of the subject on the image of the derivation region according to the present disclosure.

Then, in Step S156, the control unit 80 determines whether to perform the evaluation based on the outline of the bone part image which is the second evaluation item, on the basis of the evaluation item determined in Step S150. In a case in which the evaluation based on the outline of the bone part image is not performed, the determination result in Step S156 is "No" and the process proceeds to Step S160. On the other hand, in a case in which the evaluation based on the outline of the bone part image is performed, the determination result in Step S156 is "Yes" and the process proceeds to Step S158.

In Step S158, the control unit 80 derives the evaluation value from the outline of the bone part image.

Figure 12:
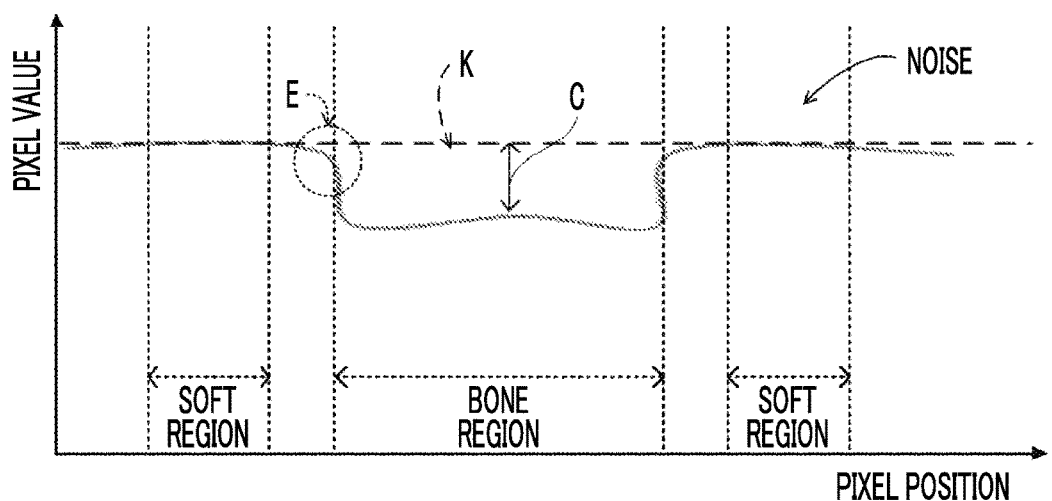
FIG. 12 is a graph illustrating an example of the DXA profile and the reference line in a case in which contrast is reduced or an edge is dulled.

In a case in which the outline of the bone part image is not clear, for example, contrast C which is a difference between the reference line K and the pixel value of the bone region in the DXA profile is low or an edge E which is the boundary of the bone region is dull as illustrated in FIG. 12. The contrast C varies depending on the influence of other factors, such as a bone mass or the body thickness of the subject W. For example, in this embodiment, a correspondence relationship among the contrast C, the degree of dullness of the edge E, and the evaluation value is obtained in advance, considering the influence of other factors. The control unit 80 detects the contrast C and the degree of dullness of the edge E from the DXA profile and derives an evaluation value corresponding to the detected contrast C and the detected degree of dullness of the edge E, on the basis of the correspondence relationship among the contrast C, the degree of dullness of the edge E, and the evaluation value. In this embodiment, the evaluation value is derived using the DXA profile derived from the DXA image. However, the evaluation value may be derived using the profile of an image corresponding to the derivation region R1 in other images. For example, the evaluation value may be derived using the profile of an image corresponding to the derivation region R1 in the first radiographic image. In addition, the correspondence relationship among the contrast C, the degree of dullness of the edge E, and the evaluation value in this embodiment is an example of an index for evaluating the clarity of the outline of an image indicating the bone in the image of the derivation region in the present disclosure.

Then, in Step S160, the control unit 80 determines whether to perform the evaluation based on the gradient of the reference line K which is the third evaluation item, on the basis of the evaluation item determined in Step S150. In a case in which the evaluation based on the gradient of the reference line K is not performed, the determination result in Step S160 is "No" and the process proceeds to Step S164. On the other hand, in a case in which the evaluation based on the gradient of the reference line K is performed, the determination result in Step S160 is "Yes" and the process proceeds to Step S162.

In Step S162, the control unit 80 derives the evaluation value from the gradient of the reference line K.

In general, in a case in which the imaging part is the lumbar vertebra, the pixel value of the reference line K is regarded as a constant value even when a noise component (trend) that is not related to the image (lumbar vertebra) of the subject W is generated. However, in some cases, the reference line K is inclined by the influence of, for example, gas or scattered rays.

Figure 13:
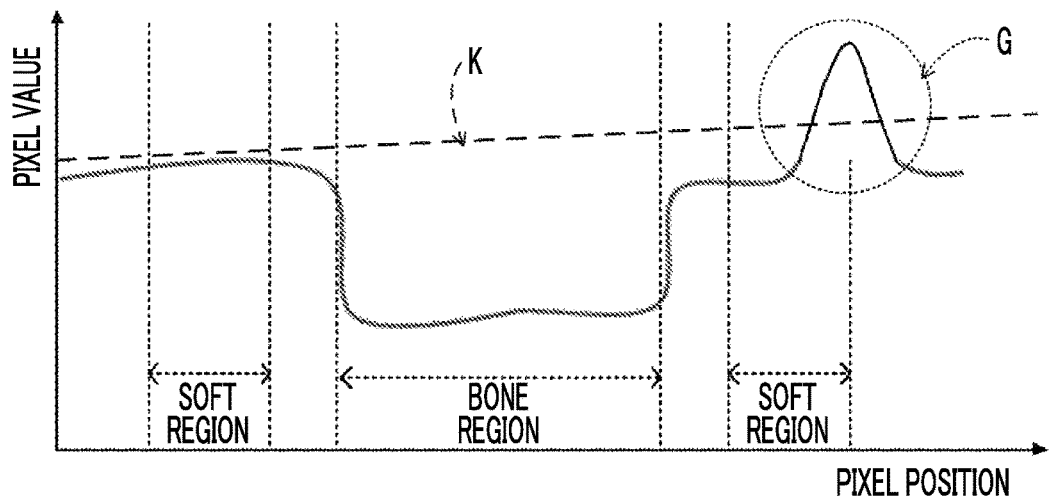
FIG. 13 is a graph illustrating another example of the DXA profile and the reference line in a case in which a gas region is included.

For example, in a case in which gas is included in the image of the derivation region R1 and the amount of gas is large, the gas region G is included in the soft region of the DXA profile as illustrated in FIG. 13. As a result, the average value of the pixel values of the soft region is greater than the average value of the pixel values of a soft region without including the gas region G. Therefore, the reference line K is inclined.

Figure 14:
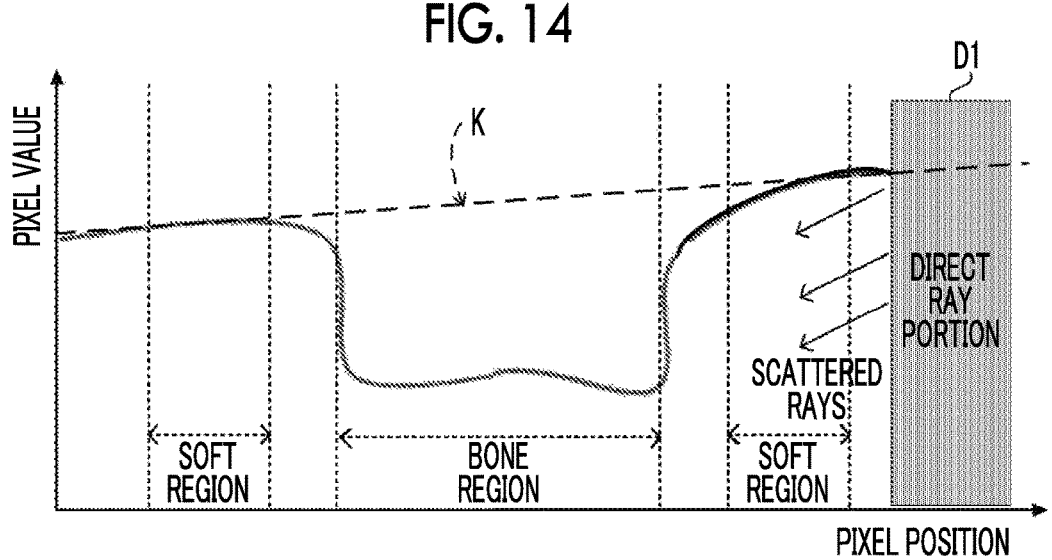
FIG. 14 is a graph illustrating an example of the DXA profile and the reference line in a case in which scattered ray components are included.

In some cases, for example, an image (a so-called omitted portion; hereinafter, referred to as a "direct ray portion") formed by direct rays of the radiation R which have reached the radiography apparatus 16 without passing through the subject W is generated in the first radiographic image and the second radiographic image. The amount of scattered rays increases due to the direct rays. Therefore, as the size of the direct ray portion increases, the influence of the scattered rays increases. For example, as illustrated in FIG. 14, since components of the scattered rays caused by the direct ray portion are superimposed on the DXA profile from the bone region to a direct ray portion D1, particularly, the soft region, the reference line K is inclined.

For this reason, for example, in this embodiment, a correspondence relationship between the gradient of the reference line K and the evaluation value is obtained in advance. The control unit 80 detects the gradient of the reference line K from the image of the derivation region R1 and derives an evaluation value corresponding to the detected gradient of the reference line K on the basis of the correspondence relationship between the gradient of the reference line K and the evaluation value. The correspondence relationship between the gradient of the reference line K and the evaluation value in this embodiment is an example of an index for evaluating the influence of gas generated in the body of the subject, from which at least one of bone density or bone mineral content is to be derived, on the image of the derivation region and an index for evaluating the influence of scattered rays of the radiation on the image of the derivation region in the present disclosure.

Figure 15:
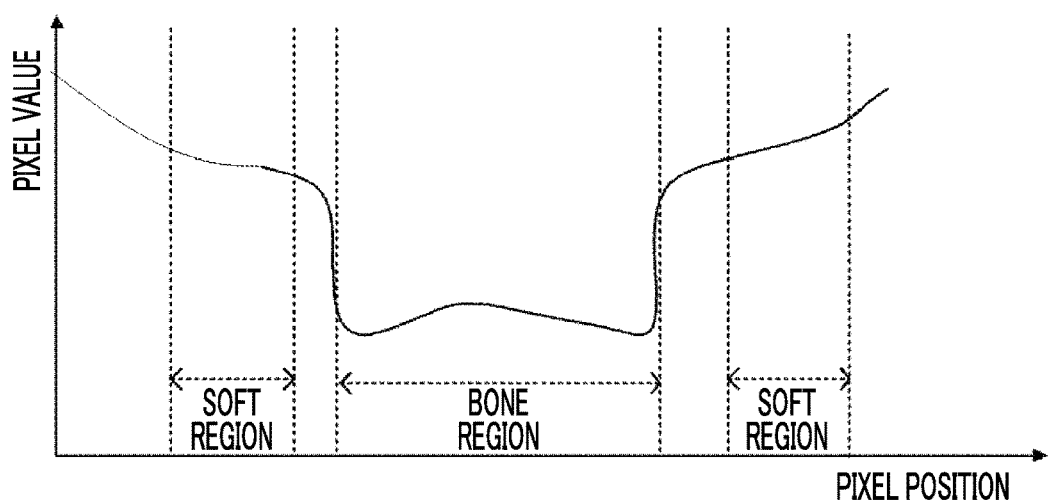
FIG. 15 is a graph illustrating an example of the DXA profile in a case in which an imaging part is the femur.

In a case in which the imaging part is the femur of the subject W, for example, the reference line is inclined in the soft region of the DXA profile due to the relationship of positioning, in addition to the influence of scattered rays, as illustrated in FIG. 15. Therefore, in a case in which the imaging part is the femur, the derivation of the reference line K subjected to fitting according to the shape of the DXA profile may be performed as a method for deriving the reference line K, unlike the above-mentioned methods. In this case, the reference line K is inclined. Therefore, the accuracy of derivation of the bone density is not necessarily low even in a case in which the reference line K is inclined. For this reason, in this embodiment, in a case in which the imaging part is the lumbar vertebra, the evaluation based on this evaluation item is performed and the process in Step S162 is performed. In a case in which the imaging part is the femur, the evaluation based on this evaluation item is not performed. Therefore, the determination result in Step S160 is "No".

Then, in Step S164, the control unit 80 determines whether to perform other predetermined evaluations which are the fourth evaluation item, on the basis of the evaluation item determined in Step S150. In a case in which other predetermined evaluations are not performed, the determination result in Step S164 is "No" and the process proceeds to Step S168. On the other hand, in a case in which other predetermined evaluations are performed, the determination result in Step S164 is "Yes" and the process proceeds to Step S166.

In Step S166, the control unit 80 performs other predetermined evaluations.

For example, as described above, as the size of the direct ray portion increases, the influence of scattered rays increases. Therefore, a correspondence relationship between the size of the direct ray portion and the evaluation value is obtained in advance. The control unit 80 detects the direct ray portion D1 from the DXA image and derives an evaluation value corresponding to the detected direct ray portion D1 on the basis of the correspondence relationship between the size of the direct ray portion and the evaluation value. In this case, the following images may be used instead of the DXA image: the first radiographic image; the second radiographic image; a bone part energy subtraction image (hereinafter, referred to as an "ES image") which has been generated using the first radiographic image and the second radiographic image and in which the bone tissues have been highlighted; and a soft part ES image which has been generated using the first radiographic image and the second radiographic image and in which the soft tissues have been highlighted. The bone part ES image in this embodiment is an example of a bone-part-highlighted image according to the present disclosure and the soft part ES image in this embodiment is an example of a soft-part-highlighted image according to the present disclosure. In addition, the correspondence relationship between the size of the direct ray portion and the evaluation value in this embodiment is an example of an index for evaluating the influence of scattered rays of the radiation on the image of the derivation region in the present disclosure.

For example, as described above, in a case in which the gas region G is generated in the DXA profile, a region other than the gas region G may be specified using the bone part ES image and the soft part ES image and the reference line K may be derived using the specified soft region.

It is easy to determine the bone region, regardless of whether or not the image of gas is included in the bone part ES image since the bone part ES image has a smaller pixel value than the image of gas included in the DXA image. For example, the control unit 80 subtracts image data obtained by multiplying the first radiographic image data by a predetermined coefficient for the bone from image data obtained by multiplying the second radiographic image data by the predetermined coefficient for the bone for each corresponding pixel to remove the soft tissues and generates bone part ES image data indicating the bone part ES image in which the bone tissues have been highlighted. Here, it is possible to remove the image of gas from the bone part ES image or to sufficiently suppress the image of gas by adjusting the predetermined coefficient, that is, by using a coefficient (the predetermined coefficient for the bone) corresponding to the influence of gas. Since the soft part ES image is an image in which the image of gas is easily seen, it is easy to avoid the gas region G. Therefore, the bone region is derived on the basis of the bone part ES image and a region other than the bone region derived on the basis of the bone part ES image and the gas region G is specified as the soft region. However, as the width of the gas region G increases and as the number of gas regions G increases, the region that can be used as the soft region is narrowed. Therefore, the accuracy of derivation of the reference line K is reduced.

As described above, since the coefficient used to generate the bone part ES image relates to the influence of gas, the correspondence relationship between the coefficient used to generate the bone part ES image and the evaluation value is obtained in advance. The control unit 80 can derive an evaluation value corresponding to the coefficient used to generate the bone part ES image from the obtained correspondence relationship. In this case, the correspondence relationship between the coefficient used to generate the bone part ES image and the evaluation value is an example of an index for evaluating the influence of gas generated in the body of the subject W, from which at least one of bone density or bone mineral content is to be derived, on the image of the derivation region in the present disclosure.

Then, in Step S168, the control unit 80 adds up the evaluation values derived by the above-mentioned process, performs normalization on the basis of 100 points, ends the evaluation value derivation process, and proceeds to Step S108 of the image processing. In addition, in a case in which the control unit 80 adds up the evaluation values, the control unit 80 may perform weighting according to, for example, the evaluation item or an evaluation method and add up the evaluation values.

In Step S108, the control unit 80 determines whether there is an evaluation item with an evaluation value equal to or less than a first threshold value in the evaluation value derivation process of Step S106. In this embodiment, the first threshold value is predetermined according to the desired accuracy of derivation. In a case in which there is an evaluation item with an evaluation value equal to or less than the first threshold value among the four evaluation items in the evaluation derivation process, the accuracy of derivation is considered not to be the desired accuracy. In a case in which there is an evaluation item with an evaluation value equal to or less than the first threshold value, the determination result in Step S108 is "No" and the process proceeds to Step S114. On the other hand, in a case in which there is no evaluation item with an evaluation value equal to or less than the first threshold value, the determination result in Step S108 is "Yes" and the process proceeds to Step S110.

In Step S110, the control unit 80 determines whether the evaluation value finally obtained by the evaluation value derivation process of Step S106 is equal to or less than a second threshold value. In this embodiment, the second threshold value is predetermined according to the desired accuracy of derivation. In a case in which the evaluation value normalized on the basis of 100 points is equal to or less than the second threshold value, the accuracy of derivation is considered not to be the desired accuracy. In a case in which the evaluation value is equal to or less than the second threshold value, the determination result in Step S110 is "Yes" and the process proceeds to Step S112.

Figure 16:
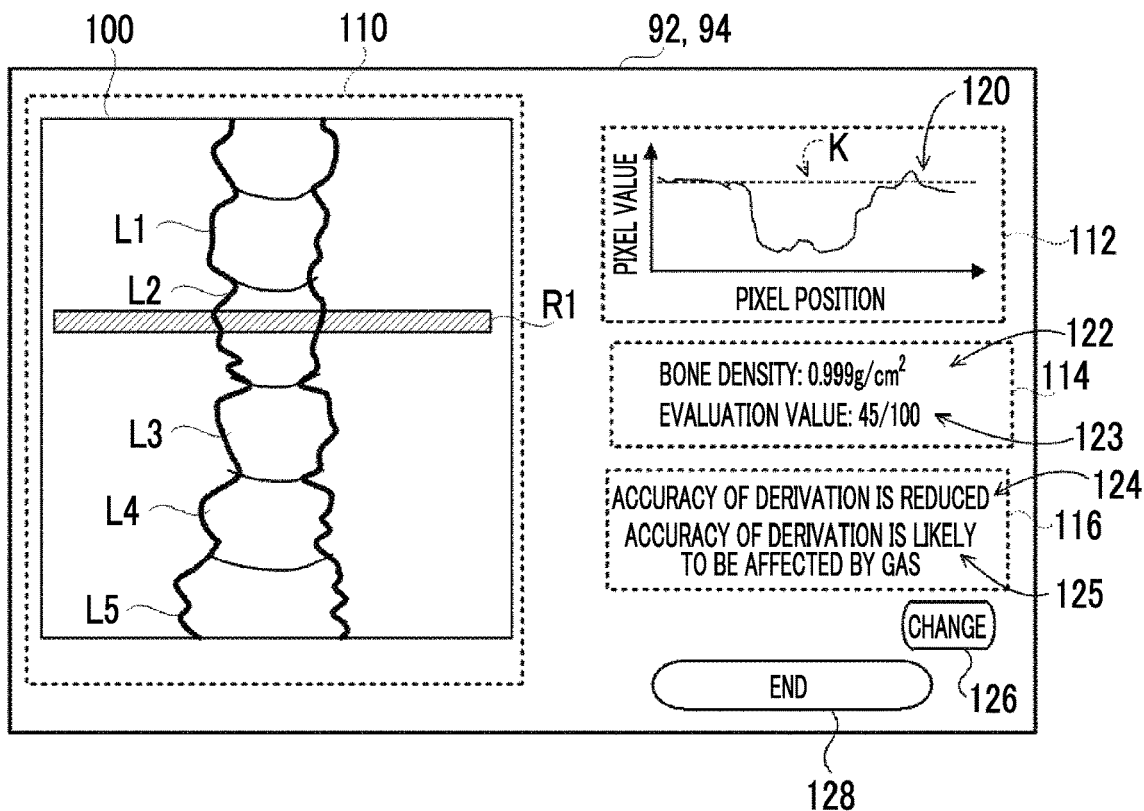
FIG. 16 is a diagram illustrating an example of the display state of bone density, an evaluation value, and a warning on a display unit in a case in which the accuracy of derivation is lower than the desired accuracy.

In Step S112, the control unit 80 displays the bone density, the evaluation value, and a warning indicating that the accuracy of derivation is lower than the desired accuracy on the display unit 92. FIG. 16 is a diagram illustrating an example of a state in which the bone density, the evaluation value, and the warning are displayed on the display unit 92. In the example illustrated in FIG. 16, the control unit 80 further displays a DXA image 100 and a DXA profile 120 on the display unit 92.

FIG. 16 illustrates a state in which the DXA image 100 is displayed in an image display region 110. As illustrated in FIG. 16, an image indicating the derivation region R1 used to derive the bone density is displayed so as to be superimposed on the DXA image 100. In addition, in the example illustrated in FIG. 16, a DXA profile used to derive the bone density is displayed in a profile display region 112.

In addition, FIG. 16 illustrates a state in which bone density information 122 indicating the bone density derived in Step S104 and evaluation value information 123 indicating the evaluation value derived in Step S106 are displayed in a bone density display region 114. In this embodiment, as an example of the evaluation value information 123, the evaluation value is displayed on the left side of "/" and information indicating full marks is displayed on the right side of "/" in FIG. 16.

Furthermore, FIG. 16 illustrates a state in which derivation accuracy reduction information 124 as an example of the warning indicating that the accuracy of derivation is low and guidance information 125 are displayed in a warning display region 116. The derivation accuracy reduction information 124 indicates that the accuracy of derivation of the bone density indicated by the bone density information 122 is low. The guidance information 125 indicates predetermined guidance for increasing the evaluation point according to the evaluation method or the evaluation item with a small evaluation point in the evaluation value derivation process (see FIG. 9). In this embodiment, the guidance information 125 for increasing the evaluation point is predetermined for each evaluation item or each evaluation method and the correspondence relationship therebetween is stored as the guidance correspondence information 89 in the storage unit 88 in advance. For example, in a case in which the evaluation item or the evaluation method is used to evaluate the influence of gas, the evaluation point is reduced due to the generation of gas. Therefore, information indicating that gas has been generated may be used as the guidance information. The control unit 80 performs a control process of displaying the guidance information 125 corresponding to the evaluation method or the evaluation item with a small evaluation point in the warning display region 116 on the basis of the guidance correspondence information 89. The guidance information 125 according to this embodiment is an example of predetermined information for increasing the evaluation value in the present disclosure.

As illustrated in FIG. 16, a change button 126 and an end button 128 are displayed on the display unit 92. The end button 128 is designated by the user through the operation unit 94 in a case in which the display of the bone density information 122 or the DXA image 100 ends.

The change button 126 is designated by the user through the operation unit 94 in a case in which the derivation region R1 is changed and bone density is derived again. In the example illustrated in FIG. 16, bone density is derived from the derivation region R1 corresponding to the second lumbar vertebra L2 and the accuracy of derivation of the bone density is low since a large amount of gas is generated in the derivation region R1 or in the vicinity of the derivation region R1. For example, in a case in which no gas generated in the fourth lumbar vertebra L4, the accuracy of derivation of the bone density in the fourth lumbar vertebra L4 is likely to satisfy the desired accuracy. In this case, according to the console 18 of this embodiment, the user who has performed determination on the basis of, for example, the DXA image 100 can designate the change button 126 to change the position (the bone whose density is to be derived) of the derivation region R1.

Then, in Step S116, the control unit 80 determines whether to change the derivation region R1. In a case in which the end button 128 displayed on the display unit 92 is designated by the user, the determination result in Step S116 is "No" and the image processing ends. On the other hand, in a case in which the change button 126 displayed on the display unit 92 is designated by the user, the determination result in Step S116 is "Yes" and the process proceeds to Step S118.

In Step S118, the control unit 80 detects a region which has been designated as the derivation region R1 by the user through the operation unit 94 and returns to Step S104. How the user designates a region as the derivation region R1 and a method for detecting the region designated by the user are not particularly limited.

For example, in a case in which the display unit 92 and the operation unit 94 are integrated into a touch panel display, the user may trace the image displayed in the image display region 110 with a finger to designate a region as the derivation region R1. In this case, for example, the control unit 80 may detect the position of the image traced by the finger of the user and may detect an image (pixel) region in a predetermined range from the detected position as the derivation region R1.

In this way, the control unit 80 derives bone density again, using the region designated by the user as the derivation region R1, and evaluates the accuracy of derivation of the bone density.

On the other hand, in a case in which the evaluation value is greater than the second threshold value, the determination result in Step S110 is "No" and the process proceeds to Step S118.

Figure 17:
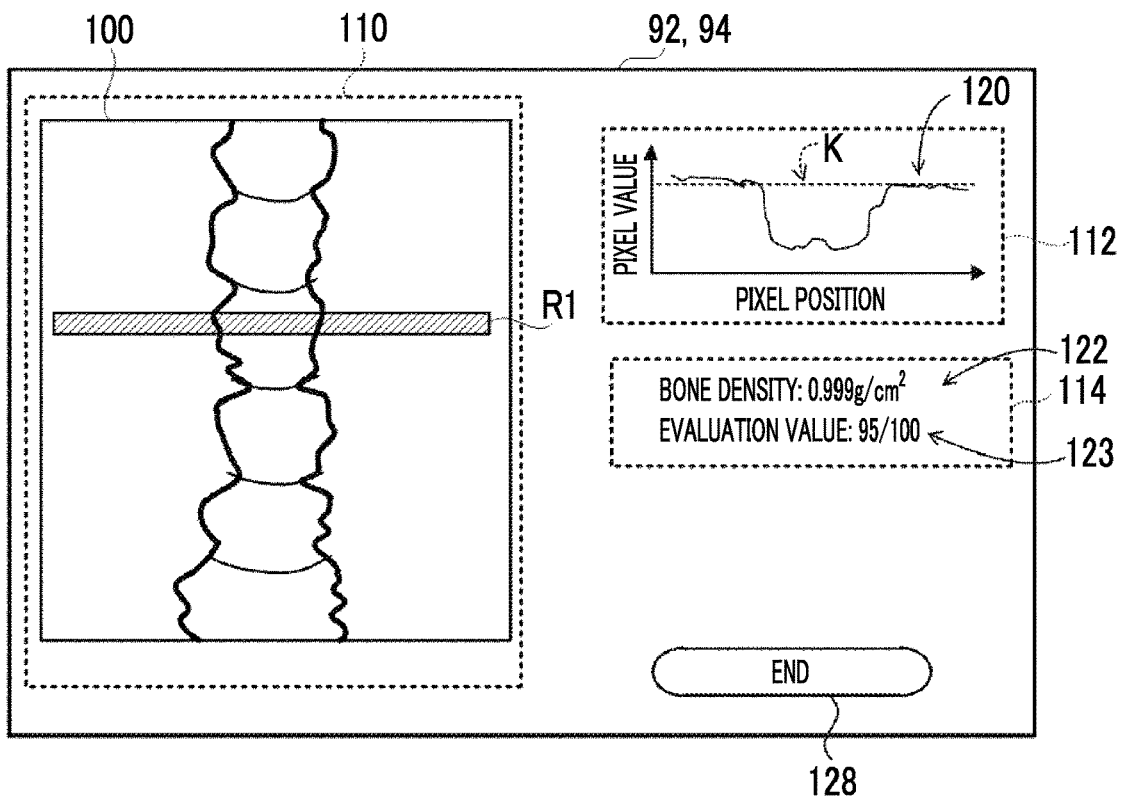
FIG. 17 is a diagram illustrating an example of the display state of bone density and an evaluation value on a display unit in a case in which the accuracy of derivation is higher than the desired accuracy.

In Step S118, the control unit 80 displays the bone density and the evaluation value on the display unit 92. FIG. 17 is a diagram illustrating an example of a state in which the bone density and the evaluation value are displayed on the display unit 92. The example illustrated in FIG. 17 differs from the display in Step S112 (see FIG. 16) in a case in which the accuracy of derivation is lower than the desired accuracy in that the warning display region 116 is not provided, the derivation accuracy reduction information 124 and the guidance information 125 are not displayed, and the change button 126 is not displayed.

Then, in Step S120, the control unit 80 determines whether to end the image processing. Until the change button 126 is designated by the user, the determination result in Step S122 is "No" and the control unit 80 is a standby state. On the other hand, in a case in which the end button 128 is designated by the user, the determination result in Step S122 is "Yes" and the control unit 80 ends the image processing.

The case in which the determination result in Step S108 of the image processing (see FIG. 8) in this embodiment is "No" and the determination result in Step S110 is "No" corresponds to an example of a case in which a condition indicating that the accuracy of derivation is high is satisfied in the present disclosure. Each of the case in which the determination result in Step S108 of the image processing in this embodiment is "Yes" and the case in which the determination result in Step S110 is "Yes" corresponds to an example of a case in which a condition indicating that the accuracy of derivation is low is satisfied in the present disclosure.

Second Embodiment

In the first embodiment, in a case in which the accuracy of derivation is lower than the desired accuracy, bone density is derived from the derivation region R1 designated by the user again and the accuracy of derivation of the bone density is evaluated. However, in this embodiment, in a case in which the accuracy of derivation is lower than the desired accuracy, the console 18 (control unit 80) automatically changes the derivation region R1, derives bone density from the changed derivation region R1 again, and evaluates the accuracy of derivation of the bone density.

Since the configuration of a radiography system 10 according to this embodiment is the same as that of the radiography system 10 (see FIGS. 1 to 4) according to the first embodiment, the description thereof will not be repeated. In this embodiment, since image processing performed by the control unit 80 of the console 18 is partially different from the image processing (see FIG. 8) according to the first embodiment, the image processing performed by the control unit 80 according to this embodiment will be described.

Figure 18:
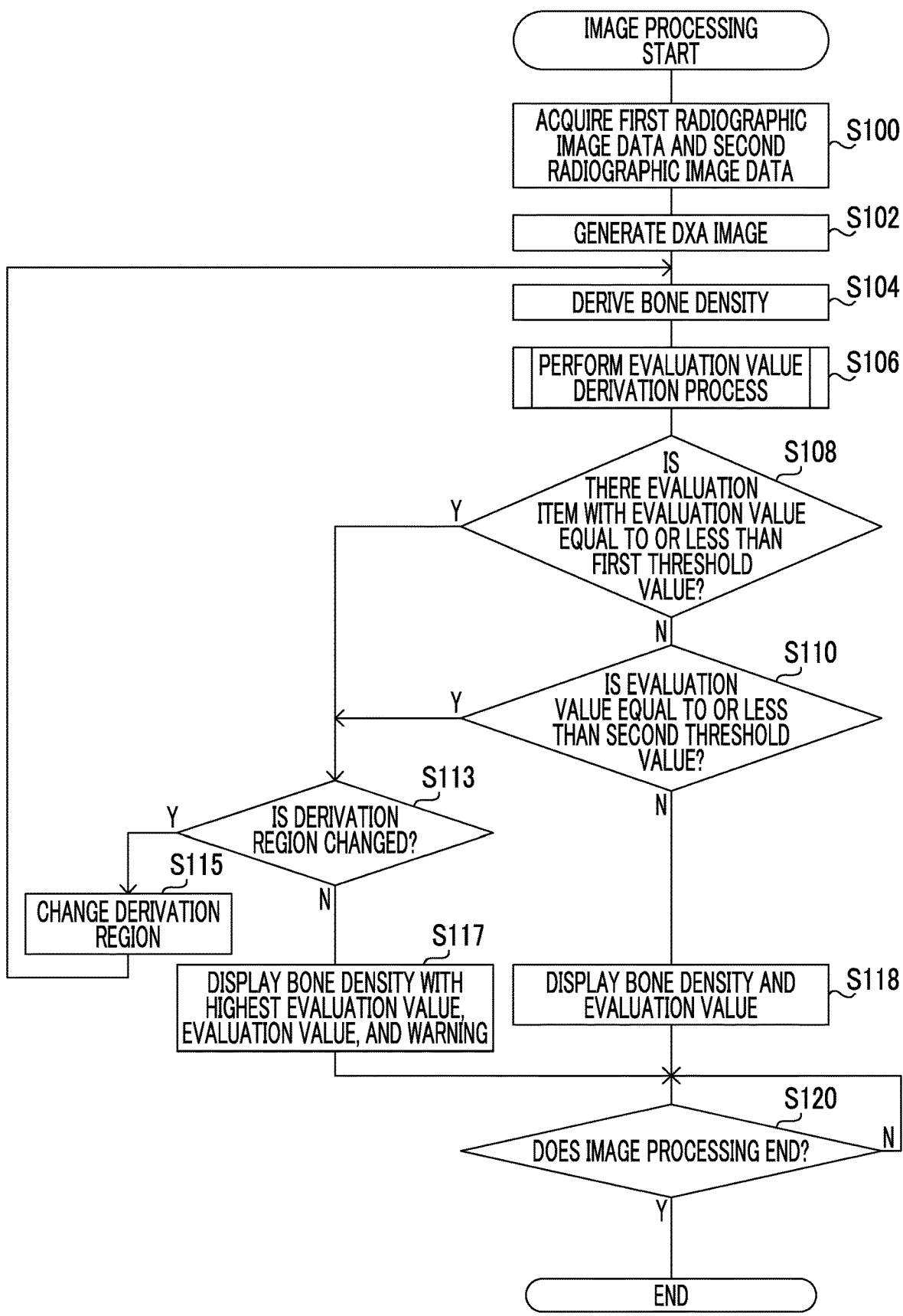
FIG. 18 is a flowchart illustrating an example of the flow of image processing performed by a control unit of a console according to a second embodiment.

FIG. 18 is a flowchart illustrating an example of the flow of the image processing performed by the control unit 80 of the console 18 according to this embodiment. As illustrated in FIG. 18, the image processing according to this embodiment is different from the image processing (see FIG. 8) according to the first embodiment in that Steps S113 to S117 are performed instead of Steps S112 to S116.

In this embodiment, as illustrated in FIG. 18, in a case in which the determination result in Step S108 is "No", the process proceeds to Step S113. In Step S113, the control unit 80 determines whether to change the derivation region R1 on the basis of the DXA image. For example, in a case in which the bone density of the second lumbar vertebra L2 is derived from the derivation region R1 corresponding to the second lumbar vertebra L2, the control unit 80 determines whether the derivation region can be changed to the derivation region R1 corresponding to each of other lumbar vertebrae, such as the first lumbar vertebra L1, the third lumbar vertebra L3, and the fourth lumbar vertebra L4.

In this embodiment, for example, in a case in which there is a lumbar vertebra whose bone density has not been derived, the determination result in Step S113 is "Yes" and the process proceeds to Step S115. In Step S115, the control unit 80 selects one lumbar vertebra whose bone density has not been derived, changes the derivation region to the derivation region R1 corresponding to the selected lumbar vertebra, and returns to Step S104. Then, the control unit 80 derives bone density again, using the changed derivation region R1, and evaluates the accuracy of derivation of the bone density.

In contrast, in a case in which the bone densities of all of the lumbar vertebrae have been derived, the determination result in Step S113 is "No" and the process proceeds to Step S117.

Figure 19:
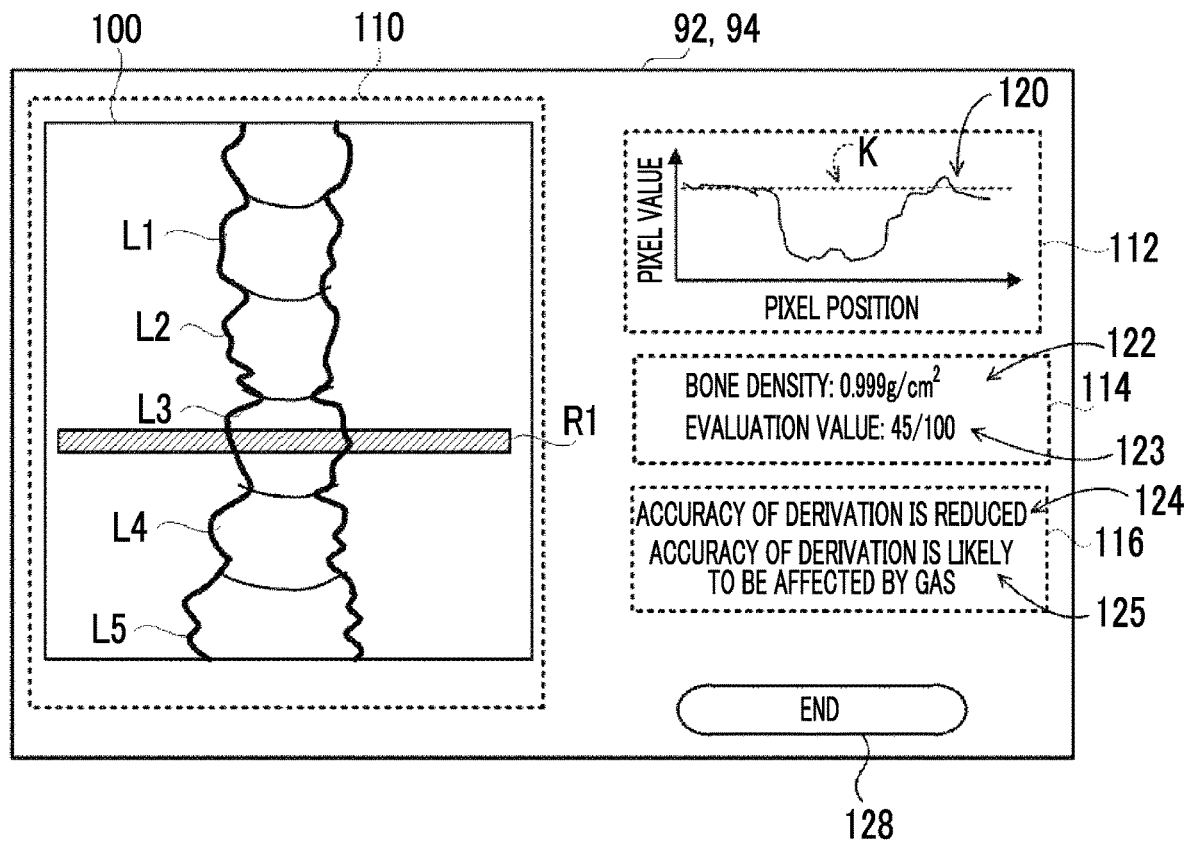
FIG. 19 is a diagram illustrating an example of the display state of bone density, an evaluation value, and a warning on a display unit in a case in which the accuracy of derivation is lower than the desired accuracy.

In Step S117, the control unit 80 displays the bone density with the maximum evaluation value among the derived bone densities, the evaluation value of the bone density, and a warning indicating that the accuracy of derivation is lower than the desired accuracy on the display unit 92. FIG. 19 is a diagram illustrating an example of a state in which the bone density, the evaluation value, and the warning are displayed on the display unit 92 in this embodiment. In addition, FIG. 19 illustrates a display state in which the accuracy of derivation of the bone density of the third lumbar vertebra L3 is the highest.

The example illustrated in FIG. 19 differs from the display in Step S112 (see FIG. 16) of the image processing (see FIG. 8) in the first embodiment in a case in which the accuracy of derivation is lower than the desired accuracy in that the change button 126 is not displayed.

Step S117 in this embodiment is performed in a case in which the accuracy of derivation of the bone density does not reach the desired accuracy even though the derivation region R1 is changed. Therefore, unlike the first embodiment, the change button 126 is not displayed.

For example, in a case in which a large amount of gas is generated and the gas is included in the entire DXA image, the accuracy of derivation of the bone density may not reach the desired accuracy. In this case, it is preferable that the image of the subject W is captured again and bone density is derived from newly captured first and second radiographic images, if necessary. In this embodiment, the user can determine whether to perform a re-imaging operation on the basis of the derivation accuracy reduction information 124 and the guidance information 125 displayed in the warning display region 116.

In addition, this embodiment may be combined with the first embodiment.

Third Embodiment

In this embodiment, a difference between an evaluation value derivation process performed by a control unit 80 of a console 18 and the evaluation value derivation process (see FIG. 9) according to each of the above-described embodiments will be described. Since the configuration of a radiography system 10 according to this embodiment is the same as that of the radiography system 10 (see FIGS. 1 to 4) according to the first embodiment, the description thereof will not be repeated.

Figure 20:
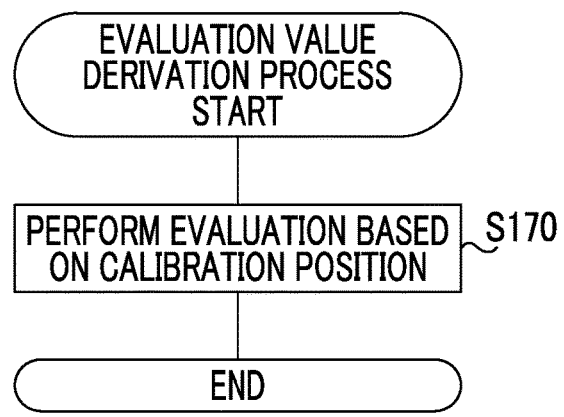
FIG. 20 is a flowchart illustrating an example of the flow of an evaluation value derivation process performed by a control unit of a console according to a third embodiment.

FIG. 20 is a flowchart illustrating an example of the flow of the evaluation value derivation process performed by the control unit 80 of the console 18 according to this embodiment.

As illustrated in FIG. 20, in the evaluation value derivation process according to this embodiment, in Step S170, the control unit 80 performs evaluation based on a calibration position and ends the evaluation value derivation process. In addition, in this embodiment, the evaluation in Step S170 is certainly performed, regardless of an imaging part.

In general, for example, the dark current or sensitivity of the radiation detector 20 varies depending on a change in surrounding environments (for example, temperature and humidity) or a change in performance over time. In order to prevent a reduction in the accuracy of derivation of the bone density, as a calibration process, radiation is emitted from the radiation emitting apparatus 12 (radiation source 14) in a state in which the subject W is absent and calibration data generated by the radiography apparatus 16 is acquired. Then, the first radiographic image and the second radiographic image are corrected on the basis of the calibration data. The calibration data according to this embodiment is an example of correction data according to the present disclosure.

In a case in which the imaging conditions of the radiography system 10 when the first radiographic image and the second radiographic image are captured are different from the imaging conditions of the radiography system 10 when calibration is performed, the first radiographic image and the second radiographic image are not appropriately corrected even though they are corrected on the basis of the calibration data. The imaging conditions of the radiography system 10 include, for example, a relative positional relationship between the radiation source 14 and the center of the radiation detector 20 and a source image distance (SID). In a case in which the first radiographic image and the second radiographic image are not appropriately corrected, the accuracy of derivation of the bone density is reduced.

For this reason, in this embodiment, the evaluation value of the accuracy of derivation of the bone density is derived on the basis of the deviation (hereinafter, referred to as "the deviation of a calibration position") between a relative position (hereinafter, referred to as a "calibration position") between the radiation source 14 and the center of the radiation detector 20 when calibration is performed and a relative position (hereinafter, referred to as an "imaging position") between the radiation source 14 and the center of the radiation detector 20 when the first radiographic image and the second radiographic image are captured.

A method for detecting the deviation of the calibration position in the control unit 80 is not particularly limited. For example, when calibration is performed and when the first radiographic image and the second radiographic image are captured, the control unit 80 captures an image of a marker disposed at a predetermined position and derives an evaluation value indicating that, as the amount of positional deviation of the marker is reduced, the accuracy of derivation increases. In this case, the control unit 80 detects the image of the marker from each of the image indicated by the calibration data and the first and second radiographic images and detects the amount of positional deviation of the image of the marker.

In addition, an image used to detect the calibration position and the imaging position is not limited to the radiographic image. For example, an image captured by a digital camera that performs general imaging with visible light may be used. In addition, the calibration position and the imaging position may be detected by a position sensor such as a potentiometer.

In a case in which the amount of deviation of the calibration position is large, the first radiographic image and the second radiographic image are not appropriately corrected as described above, which results in a reduction in the accuracy of derivation of the bone density. For this reason, it is preferable to capture the image of the subject W again or to perform calibration (hereinafter, generically referred to as "re-imaging") based on the calibration position aligned with the imaging position. Therefore, the guidance information 125 for guiding the execution of re-imaging is associated with the evaluation of the calibration position in the guidance correspondence information 89 stored in the storage unit 88 in this embodiment.

Since the evaluation value derivation process is performed in this way, the control unit 80 of the console 18 according to this embodiment derives the evaluation value on the basis of the deviation of the calibration position detected from the first radiographic image, the second radiographic image, and the image indicated by the calibration data and determines whether the desired accuracy of derivation is satisfied.

In addition, this embodiment may be combined with each of the above-described embodiments. For example, in a case in which this embodiment is combined with the first embodiment, the evaluation items used by the control unit 80 to evaluate the accuracy of derivation in the evaluation value derivation process may be five evaluation items, that is, the four evaluation items described in the evaluation value derivation process (see FIG. 9) according to the first embodiment and the evaluation based on the calibration position described in this embodiment.

Figure 21:
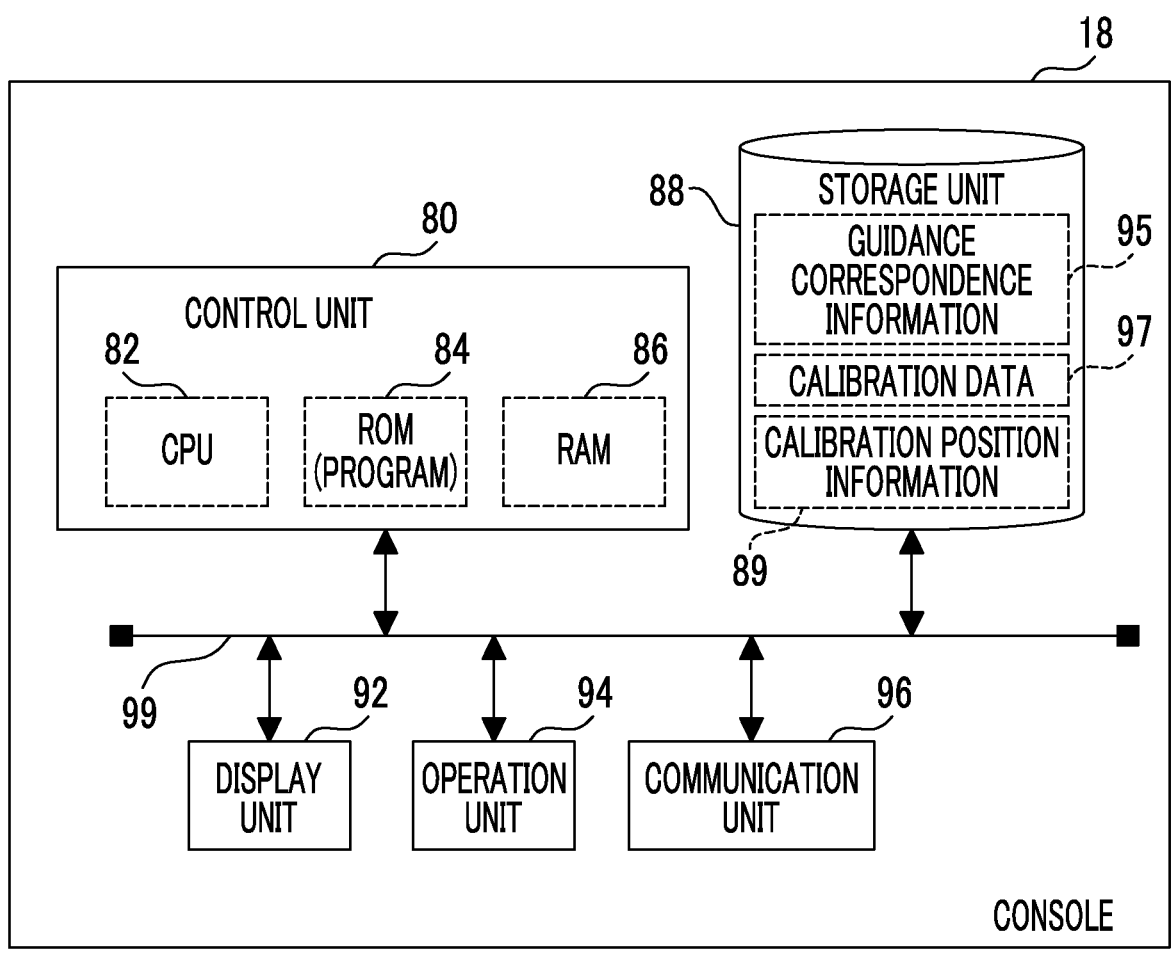
FIG. 21 is a block diagram illustrating another example of the configuration of a main portion of an electric system of the console according to the third embodiment.

For example, a weight for the evaluation based on the calibration position may be greater than a weight for the evaluation based on other evaluation items. In this case, the evaluation based on the calibration position may be performed before the evaluation based on other evaluation items. In this case, as illustrated in FIG. 21, the control unit 80 of the console 18 acquires calibration data 95 and calibration position information 97 as information indicating the imaging conditions when calibration for acquiring the calibration data 95 is performed from the radiography apparatus 16 and stores the acquired data and information in the storage unit 88 in advance.

Figure 22:
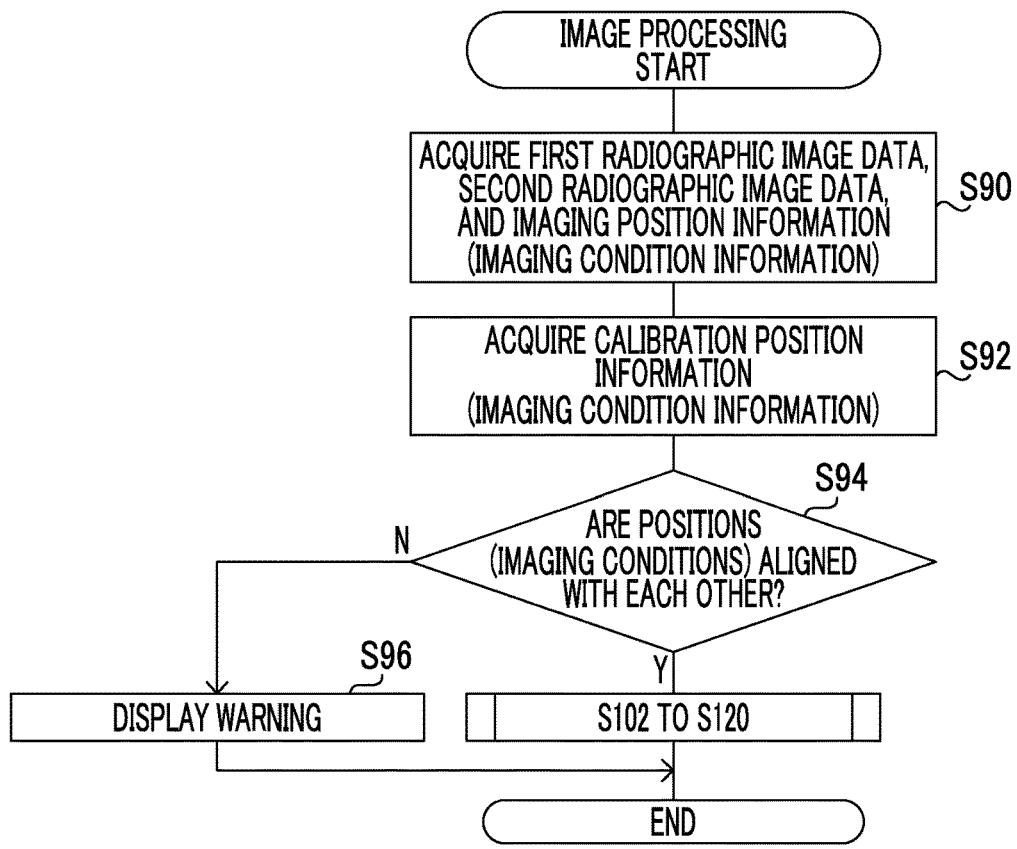
FIG. 22 is a flowchart illustrating another example of the flow of image processing performed by a control unit of the console according to the third embodiment.

FIG. 22 is a flowchart illustrating an example of the flow of image processing performed by the control unit 80.

The image processing illustrated in FIG. 22 differs from the image processing (see FIG. 8) according to the first embodiment in that Steps S90 to S96 are performed instead of Step S100.

In Step S90 of the image processing illustrated in FIG. 22, the control unit 80 acquires the first radiographic image data, the second radiographic image, and information indicating the imaging position as the imaging condition from the radiography apparatus 16.

Then, in Step S92, the control unit 80 acquires the calibration position information 97 from the storage unit 88.

Then, in Step S94, the control unit 80 determines whether the imaging position and the calibration position (imaging conditions) are aligned with each other, on the basis of the imaging position information (imaging condition information) acquired in Step S90 and the calibration position information 97 acquired in Step S92. In a case in which the amount of deviation between the imaging position and the calibration position is equal to or less than the amount of deviation in which the accuracy of derivation of the bone density is evaluated to satisfy the desired accuracy, the control unit 80 considers that the calibration position and the imaging position are aligned with each other. The determination result in Step S94 is "Yes" and the process proceeds to Step S102 of the image processing (see FIG. 8) according to the first embodiment.

Figure 23:
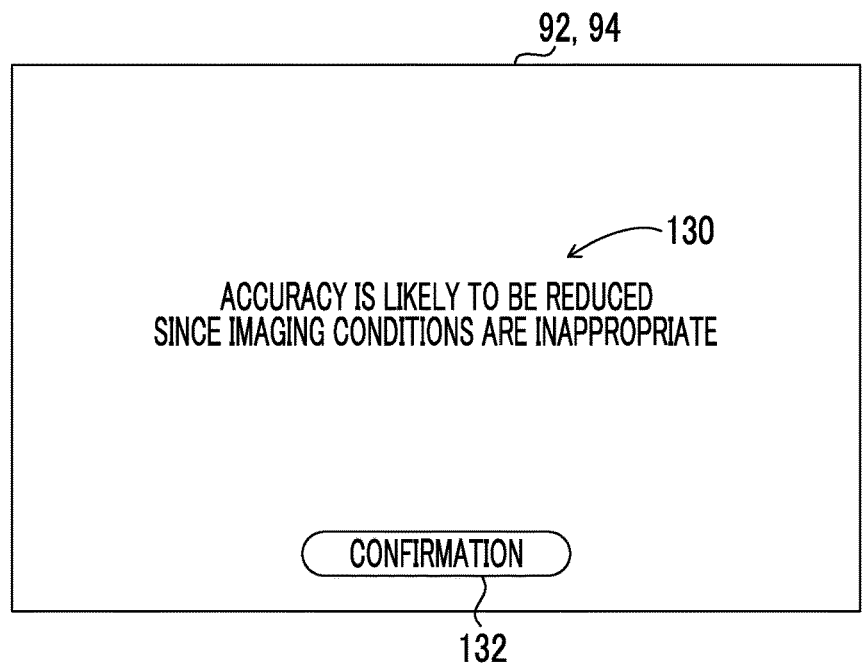
FIG. 23 is a diagram illustrating an example of the display state of a warning on the display unit in a case in which a calibration position deviates.

On the other hand, in a case in which the determination result in Step S94 is "No", the process proceeds to Step S96. In Step S96, the control unit 80 controls the display unit 92 such that a predetermined warning is displayed on the display unit 92 and proceeds to Step S120. FIG. 23 is a diagram illustrating an example of a state in which a warning is displayed on the display unit 92. FIG. 23 illustrates a state in which warning information 130 indicating that the accuracy of derivation is likely to be reduced since the calibration position deviates and a confirmation button 132 are displayed on the display unit 92. The user can see the display of the warning information 130 and rapidly perform a re-imaging operation for the subject W or perform calibration based on the calibration position aligned with the imaging position.

In the example illustrated in FIG. 23, in a case in which the user designates the confirmation button 132 through the operation unit 94, the determination result in Step S122 is "Yes" and the image processing ends.

As such, in the image processing illustrated in FIG. 22, in a case in which the amount of deviation of the calibration position is large, it is clear that the accuracy of derivation of the bone density does not satisfy the desired accuracy. For this reason, in this case, the control unit 80 does not derive bone density and displays the warning information 130 of the display unit 92. Therefore, it is possible to reduce the processing load of the control unit 80 and to prompt the user to make a quick response.

In the above description, the control unit 80 performs determination on the basis of the amount of deviation of the calibration position. However, the criterion is not limited to the amount of deviation of the calibration position. The evaluation may be performed on the basis of a difference in other imaging conditions. For example, the evaluation may be performed on the basis of a tube voltage, the amount of deviation of SID, the size of the irradiation field, and the positioning state of the subject W as the imaging conditions. For example, in a case in which the position of a bone part image in the radiographic image is in the vicinity of the outside of the irradiation field, the gap (distance) from the bone part image to the outside of the irradiation field is small and it is difficult to appropriately set the soft region. Therefore, in a case in which the size of the irradiation field is small (the size of a region outside the irradiation field is large), there is a concern that the gap from the bone part image to the outside of the irradiation field will be small. Therefore, the evaluation value may be reduced. For example, in calibration, in a case in which the bone part image is located at the center of the image, the accuracy of derivation is the highest. Therefore, in a case in which the bone part image is located outside the vicinity of the center of the radiographic image, there is a concern that the accuracy of derivation will be reduced. For this reason, in a case in which the bone part image is located outside the vicinity of the center of the image, the evaluation value may be reduced. In a case in which the backbone is bent, for example, in the case of scoliosis, the bone part image is located outside the vicinity of the center of the image and the gap between the bone part image and the outside of the irradiation field is small. Therefore, the evaluation value may be reduced.

As described above, in each of the above-described embodiments, the control unit 80 of the console 18 acquires the first radiographic image data and the second radiographic image data and derives bone density from the image of the derivation region R1 of the DXA image which is a difference image between the first radiographic image and the second radiographic image. Then, the control unit 80 derives the evaluation value of the accuracy of derivation of the bone density, on the basis of at least one of the first radiographic image, the second radiographic image, and the bone part ES image, the soft part ES image, and the DXA image generated using the first radiographic image and the second radiographic image.

For example, in some cases, the pixel value of the DXA image indicated by the DXA image data is inappropriate due to the influence of noise or gas generated in the body of the subject is included in the radiographic image (DXA image). In a case in which bone density or bone mineral content is derived in this state, the accuracy of the derived bone density or bone mineral content is reduced.

As such, in each of the above-described embodiments, the control unit 80 derives the evaluation value of the accuracy of derivation of the bone density. Therefore, in a case in which the accuracy of derivation is low, for example, it is possible to rapidly perform a process for increasing the accuracy of derivation. For example, a predetermined process may be performed for image data, such as DXA image data, or radiographic images may be captured again.

Therefore, according to the console 18 of each of the above-described embodiments, it is possible to improve the accuracy of derivation of the bone density.

For example, the configuration and operation of the radiography system 10, the radiography apparatus 16, and the console 18 described in each of the above-mentioned embodiments are illustrative and can be changed according to situations, without departing from the scope and spirit of the invention.

For example, the evaluation item or the evaluation method for evaluating the accuracy of derivation is not limited to that described in each of the above-described embodiments. For example, in a case in which the user designates a reference soft region for deriving the reference line K through the operation unit 94 and actually designates the soft tissues in a region corresponding to the bone tissues, the evaluation value of the accuracy of derivation may be reduced (deducted).

In addition, the control unit 80 may derive bone density using a plurality of derivation regions R1. For example, the control unit 80 may derive the bone density of each of five lumbar vertebrae from the first lumbar vertebra to the fifth lumbar vertebra, using the derivation regions R1 corresponding to the five lumbar vertebrae, derive the accuracy of derivation, and derive the average value of the bone densities of the lumbar vertebrae as the bone density of the subject W. In this case, the control unit 80 may derive, as the bone density of the subject W, the average value of the bone densities except the bone density of the lumbar vertebra whose derivation accuracy is the lowest or the bone density of the lumbar vertebra from which the evaluation value that does not satisfy the desired accuracy has been derived. In addition, the control unit 80 may display the evaluation value for each lumbar vertebra (for each derivation region R1) on the display unit 92.

Figure 24:
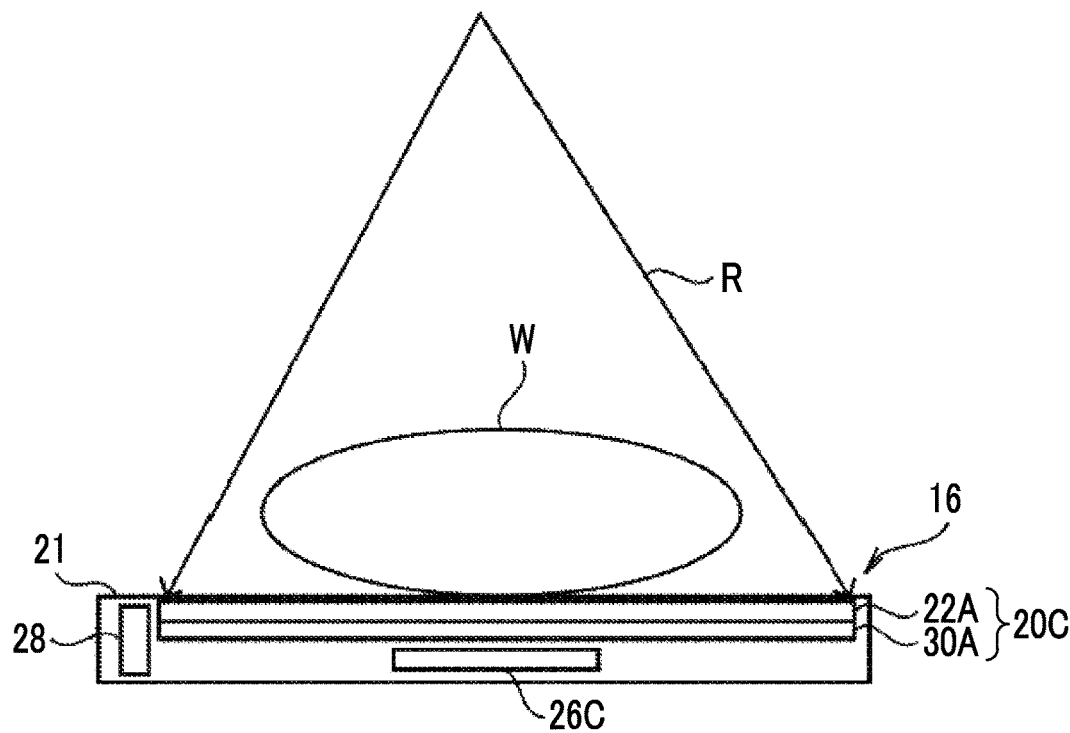
FIG. 24 is a side cross-sectional view illustrating another example of the configuration of the radiography apparatus.

For example, in the above-described embodiments, the radiography apparatus 16 includes two radiation detectors. However, for example, as illustrated in FIG. 24, the radiography apparatus 16 may include a single radiation detector. In the example illustrated in FIG. 24, a radiation detector 20C that detects the radiation R transmitted through the subject W and a control substrate 26C are provided in the housing 21 of the radiography apparatus 16. The configuration of the radiation detector 20C is the same as that of the first radiation detector 20A according to the first embodiment and the configuration of the control substrate 26C is the same as that of the control substrate 26A according to the first embodiment. Therefore, the description thereof will not be repeated here.

In the radiography apparatus 16 illustrated in FIG. 24, two radiography operations are performed at different tube voltages from the radiation emitting apparatus 12 and bone density is derived on the basis of radiographic image data captured by the radiation detector 20C in the two radiography operations. Since different tube voltages are used in the two radiography operations, the radiation detector 20C is irradiated with the radiations R having different energy levels.

Figure 25:
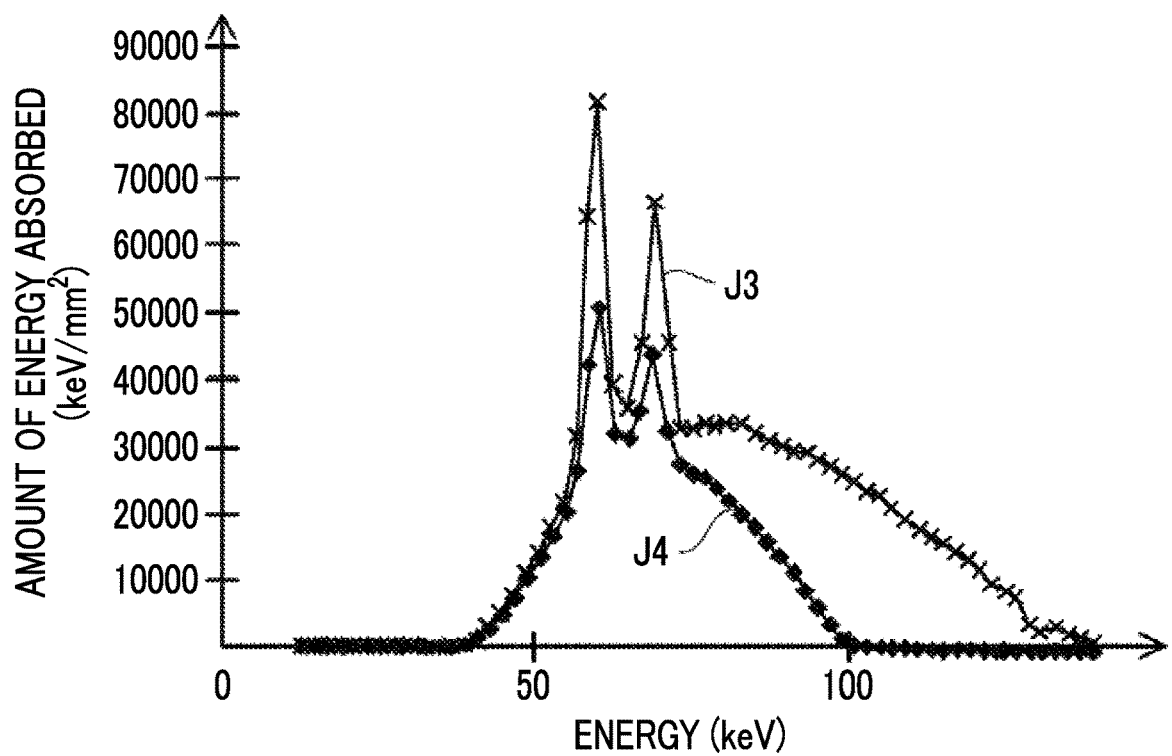
FIG. 25 is a graph illustrating the amount of radiation absorbed by a radiation detector in a case in which radiation is emitted at different tube voltages.

The radiation R absorbed by the radiation detector 20C will be described with reference to FIG. 25. In FIG. 25, the vertical axis indicates the amount of radiation R absorbed per unit area and the horizontal axis indicates the energy of the radiation R. In addition, in FIG. 25, a solid line J3 indicates the relationship between the energy of the radiation R absorbed by the radiation detector 20C and the amount of radiation R absorbed per unit area in a case in which the tube voltage of the radiation source 14 is 140 kV. In FIG. 25, a solid line J4 indicates the relationship between the energy of the radiation R absorbed by the radiation detector 20C and the amount of radiation R absorbed per unit area in a case in which the tube voltage of the radiation source 14 is 100 kV. As illustrated in FIG. 25, since the tube voltages of the radiation source 14 are different from each other, the radiation detector 20C is irradiated with the radiations R having different energy levels in first irradiation and second irradiation.

In each of the above-described embodiments, the image display process performed by the console 18 may be performed by the control unit 58A or the control unit 58B of the radiography apparatus 16. In addition, in a case in which the radiography apparatus 16 includes an overall control unit that controls the overall operation of the control unit 58A and the control unit 58B, the overall control unit may perform the bone density derivation process or the image display process. Furthermore, for example, an image processing apparatus that is connected to the console 18 through the network may perform the bone density derivation process or the image display process.

In the first embodiment, the case in which an indirect-conversion-type radiation detector that converts radiation into light and converts the converted light into charge is applied to both the first radiation detector 20A and the second radiation detector 20B has been described. However, the invention is not limited thereto. For example, a direct-conversion-type radiation detector that directly converts radiation into charge may be applied to at least one of the first radiation detector 20A or the second radiation detector 20B. In addition, for example, a conversion layer that absorbs radiation and converts the radiation into charge in the direct-conversion-type radiation detector is made of amorphous selenium (a-Se) and crystalline cadmium telluride (CdTe).

In the first embodiment, the case in which the irradiation side sampling radiation detectors in which the radiation R is incident from the TFT substrates 30A and 30B are applied to the first radiation detector 20A and the second radiation detector 20B, respectively, has been described. However, the invention is not limited thereto. For example, a so-called penetration side sampling (PSS) radiation detector in which the radiation R is incident from the scintillator 22A or 22B may be applied to at least one of the first radiation detector 20A or the second radiation detector 20B.

In each of the above-described embodiments, the case in which bone density is derived using the first radiographic image data and the second radiographic image data has been described. However, the invention is not limited thereto. For example, bone mineral content or both bone density and bone mineral content may be derived using the first radiographic image data and the second radiographic image data. In a case in which bone mineral content is derived, the evaluation value of the accuracy of derivation is derived similarly to the derivation of the bone density. In this case, the same effect as that in each of the above-described embodiments is obtained.

In each of the above-described embodiments, the image processing performed by the execution of software (program) by the CPU 82 of the control unit 80 may be performed by various processors other than the CPU 82. In this case, examples of the processor include a programmable logic device (PLD) whose circuit configuration can be changed after manufacture, such as a field-programmable gate array (FPGA), and a dedicated electric circuit, such as an application specific integrated circuit (ASIC), which is a processor having a dedicated circuit configuration designed to perform a specific process. In addition, the image processing may be performed by one of the various processors or may be performed by a combination of two or more processors of the same type or different types (for example, a combination of a plurality of FPGAs and a combination of a CPU and an FPGA). Specifically, the hardware structure of the various processors is an electric circuit obtained by combining circuit elements such as semiconductor elements.

In each of the above-described embodiments, the aspect in which the image processing program is stored (installed) in the ROM 84 in advance has been described. However, the invention is not limited thereto. The image processing program may be recorded on a recording medium, such as a compact disk read only memory (CD-ROM), a digital versatile disk read only memory (DVD-ROM), or a universal serial bus (USB) memory, and then provided. In addition, the image processing program may be downloaded from an external apparatus through the network.

What is claimed is:

1. An image processing apparatus comprising:
    an acquisition unit that acquires a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted;
    a first derivation unit that derives at least one of bone density or bone mineral content from an image of a predetermined derivation region of a difference image between the first radiographic image and the second radiographic image;
    a second derivation unit that derives an evaluation value of an accuracy of derivation of the at least one of the bone density or the bone mineral content derived by the first derivation unit, on the basis of a third radiographic image generated using the first radiographic image and the second radiographic image; and
    a display control unit that performs a control process of displaying information indicating that the accuracy of derivation is low on a display unit in a case in which the evaluation value derived by the second derivation unit satisfies a condition indicating that the accuracy of derivation is low;
    wherein, in a case in which the evaluation value derived by the second derivation unit satisfies a condition indicating that the accuracy of derivation is low, the first derivation unit derives at least one of the bone density or the bone mineral content from an image of a derivation region which is different from the derivation region used to derive the at least one of the bone density or the bone mineral content and the second derivation unit derives an evaluation value of the accuracy of derivation of the at least one of the bone density or the bone mineral content derived by the first derivation unit.

2. The image processing apparatus according to claim 1, wherein the second derivation unit derives the evaluation value on the basis of at least one of an index for evaluating noise which is superimposed on the image of the derivation region, an index for evaluating an influence of gas generated in a body of a subject, from which the at least one of the bone density or the bone mineral content is to be derived, on the image of the derivation region, or an index for evaluating an influence of scattered rays of the radiation on the image of the derivation region.

3. The image processing apparatus according to claim 1, wherein the first radiographic image and the second radiographic image are corrected by correction data which is generated by irradiating the radiography apparatus with the radiation, and
the second derivation unit derives the evaluation value on the basis of an imaging condition in a case in which the correction data is generated and an imaging condition in a case in which the first radiographic image and the second radiographic image are generated.

4. The image processing apparatus according to claim 3, wherein the imaging condition is a position of a radiation source that irradiates the radiography apparatus with the radiation.

5. The image processing apparatus according to claim 1, wherein the second derivation unit derives the evaluation value on the basis of an index for evaluating clarity of an outline of an image indicating a bone in the image of the derivation region.

6. The image processing apparatus according to claim 1, further comprising:
a display control unit that performs a control process of displaying the at least one of the bone density or the bone mineral content derived by the first derivation unit on a display unit in a case in which the evaluation value derived by the second derivation unit satisfies a condition indicating that the accuracy of derivation is high.

7. The image processing apparatus according to claim 1, wherein the display control unit further performs a control process of displaying predetermined information for increasing the evaluation value on the display unit.

8. The image processing apparatus according to claim 1, further comprising:
a display control unit that performs a control process of displaying at least one of the bone density or the bone mineral content with a higher evaluation value among the evaluation values derived by the second derivation unit on the display unit.

9. The image processing apparatus according to claim 1, wherein the third radiographic image is at least one of the difference image, a bone-part-highlighted image in which a bone tissue is highlighted, a soft-part-highlighted image in which a soft tissue is highlighted, the first radiographic image, or the second radiographic image.

10. The image processing apparatus according to claim 1, wherein each of the first and second radiation detectors comprises a light emitting layer that is irradiated with the radiation and emits light,
the plurality of pixels of each of the first and second radiation detectors receive the light, generate the charge, and accumulate the charge, and
the light emitting layer of one of the first and second radiation detectors which is provided on an incident side of the radiation includes cesium iodide (CsI) and the light emitting layer of the other radiation detector includes gadolinium oxysulfide (GOS).

11. A radiography system comprising:
the image processing apparatus according to claim 1; and
a radiography apparatus that outputs a first radiographic image and a second radiographic image to the image processing apparatus.

12. An image processing apparatus comprising:
an acquisition unit that acquires a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged;
a first derivation unit that derives at least one of bone density or bone mineral content from an image of a predetermined derivation region of a difference image between the first radiographic image and the second radiographic image;
a second derivation unit that derives an evaluation value of an accuracy of derivation of the at least one of the bone density or the bone mineral content derived by the first derivation unit, on the basis of a third radiographic image generated using the first radiographic image and the second radiographic image; and
a display control unit that performs a control process of displaying information indicating that the accuracy of derivation is low on a display unit in a case in which the evaluation value derived by the second derivation unit satisfies a condition indicating that the accuracy of derivation is low;
wherein, in a case in which the evaluation value derived by the second derivation unit satisfies a condition indicating that the accuracy of derivation is low, the first derivation unit derives at least one of the bone density or the bone mineral content from an image of a derivation region which is different from the derivation region used to derive the at least one of the bone density or the bone mineral content and the second derivation unit derives an evaluation value of the accuracy of derivation of the at least one of the bone density or the bone mineral content derived by the first derivation unit.

13. An image processing method comprising:
acquiring a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted;
deriving, by a first derivation process, at least one of bone density or bone mineral content from an image of a predetermined derivation region of a difference image between the first radiographic image and the second radiographic image;
deriving, by a second derivation process, an evaluation value of an accuracy of derivation of the at least one of the bone density or the bone mineral content, on the basis of a third radiographic image generated using the first radiographic image and the second radiographic image; and
displaying information indicating that the accuracy of derivation is low on a display unit in a case in which the evaluation value derived by the second derivation process satisfies a condition indicating that the accuracy of derivation is low;
wherein, in a case in which the evaluation value derived by the second derivation process satisfies a condition indicating that the accuracy of derivation is low, the first derivation process derives at least one of the bone density or the bone mineral content from an image of a derivation region which is different from the derivation region used to derive the at least one of the bone density or the bone mineral content and the second derivation process derives an evaluation value of the accuracy of derivation of the at least one of the bone density or the bone mineral content derived by the first derivation process.

14. An image processing method comprising:

acquiring a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged;

deriving, by a first derivation process, at least one of bone density or bone mineral content from an image of a predetermined derivation region of a difference image between the first radiographic image and the second radiographic image;

deriving, by a second derivation process, an evaluation value of an accuracy of derivation of the at least one of the bone density or the bone mineral content, on the basis of a third radiographic image generated using the first radiographic image and the second radiographic image; and displaying information indicating that the accuracy of derivation is low on a display unit in a case in which the evaluation value derived by the second derivation process satisfies a condition indicating that the accuracy of derivation is low;

wherein, in a case in which the evaluation value derived by the second derivation process satisfies a condition indicating that the accuracy of derivation is low, the first derivation process derives at least one of the bone density or the bone mineral content from an image of a derivation region which is different from the derivation region used to derive the at least one of the bone density or the bone mineral content and the second derivation process derives an evaluation value of the accuracy of derivation of the at least one of the bone density or the bone mineral content derived by the first derivation process.

* * * * *